US012344815B2

(12) United States Patent
Hariyama et al.

(10) Patent No.: US 12,344,815 B2
(45) Date of Patent: Jul. 1, 2025

(54) ODORANT COMPOSITION

(71) Applicants: NATIONAL UNIVERSITY CORPORATION HAMAMATSU UNIVERSITY SCHOOL OF MEDICINE, Shizuoka (JP); NATIONAL UNIVERSITY CORPORATION KOBE UNIVERSITY, Hyogo (JP)

(72) Inventors: Takahiko Hariyama, Hamamatsu (JP); Mamiko Ozaki, Hyogo (JP)

(73) Assignees: NATIONAL UNIVERSITY CORPORATION HAMAMATSU UNIVERSITY SCHOOL OF MEDICINE, Shizuoka (JP); NATIONAL UNIVERSITY CORPORATION KOBE UNIVERSITY, Hyogo (JP)

( * ) Notice: Subject to any disclaimer, the term of this patent is extended or adjusted under 35 U.S.C. 154(b) by 707 days.

(21) Appl. No.: 17/625,598

(22) PCT Filed: Jul. 11, 2020

(86) PCT No.: PCT/JP2020/027171
§ 371 (c)(1),
(2) Date: Jan. 7, 2022

(87) PCT Pub. No.: WO2021/010359
PCT Pub. Date: Jan. 21, 2021

(65) Prior Publication Data
US 2022/0259518 A1    Aug. 18, 2022

(30) Foreign Application Priority Data
Jul. 12, 2019 (JP) .................... 2019-129679

(51) Int. Cl.
| | |
|---|---|
| *C11B 9/00* | (2006.01) |
| *A61K 8/31* | (2006.01) |
| *A61K 8/35* | (2006.01) |
| *A61Q 13/00* | (2006.01) |
| *C09D 11/03* | (2014.01) |

(52) U.S. Cl.
CPC .............. *C11B 9/0015* (2013.01); *A61K 8/31* (2013.01); *A61K 8/35* (2013.01); *A61Q 13/00* (2013.01); *C09D 11/03* (2013.01); *A61K 2800/412* (2013.01); *A61K 2800/413* (2013.01)

(58) Field of Classification Search
CPC . C09D 11/03; A61K 8/35; A61K 8/31; A61K 2800/413; A61K 2800/412; A61D 13/00; C11B 9/00; C11B 9/0015; A23L 27/00
USPC ........................................ 512/4, 1
See application file for complete search history.

(56) References Cited

U.S. PATENT DOCUMENTS

| | | | |
|---|---|---|---|
| 2008/0311069 A1* | 12/2008 | Williams | ................. A61K 8/35 424/76.1 |
| 2018/0100121 A1* | 4/2018 | Blondeau | .............. C11B 9/0019 |

FOREIGN PATENT DOCUMENTS

| | | |
|---|---|---|
| JP | 2002-285189 | 10/2002 |
| JP | 2008-101129 | 5/2008 |

OTHER PUBLICATIONS

International Search Report issued Sep. 24, 2020 in International (PCT) Application No. PCT/JP2020/027171.
Office Action issued Jun. 27, 2024 in corresponding Chinese Patent Application No. 202080050511.8, with English language translation.
First Office Action issued Nov. 1, 2023 in corresponding Chinese Patent Application No. 202080050511.8, with English language translation.
Notice of Reasons for Refusal dated Jul. 30, 2024 in corresponding Japanese Patent Application No. 2021-533060, with English-language Translation.
Extended European Search Report issued Jul. 6, 2023 in corresponding European Patent Application No. 20839991.5.

* cited by examiner

*Primary Examiner* — Jessica Whiteley
(74) *Attorney, Agent, or Firm* — Wenderoth, Lind & Ponack, L.L.P.

(57) ABSTRACT

The present invention provides an odorant composition having good palatability allowing peoples to feel comfortable using a small number of chemical compounds. An odorant composition according to an embodiment of the present invention consists of: when the total mass of ingredients contained in the odorant composition is 100.0% by mass, 40.0% by mass or more and 97.5% by mass or less of an ingredient (A) composed of aldehydes; 1.0% by mass or more and 20.0% by mass or less of an ingredient (B) composed of a ketone(s); and the balance being an ingredient (C) composed of a chemical compound(s) other than the ingredient (A) and the ingredient (B). The aldehydes of the ingredient (A) are: an essential ingredient (A1) composed of nonanal; and an optional ingredient (A2) selected from the group consisting of decanal, heptanal, octanal, benzaldehyde, undecanal, hexanal, and combinations thereof. The ketone(s) of the ingredient (B) is selected from the group consisting of 6-methyl-5-hepten-2-one, cyclohexanone, 1-phenylethanone, 2-decanone, 2-undecanone, and combinations thereof. The chemical compound(s) of the ingredient (C) is selected from the group consisting of limonene, 1,8-cineole, menthol, 1-octanol, 3-hexyn-1-ol, 2-nonen-1-ol, dodecane, hexanoic acid, octanoic acid, nonanoic acid, 2(5H)-furanone, p-cymene, sotolon, and combinations thereof.

13 Claims, 14 Drawing Sheets

ODORANT COMPOSITION

TECHNICAL FIELD

The present invention relates to an odorant composition.

BACKGROUND ART

In recent years, various studies have been performed on psychological and physiological effects of a scent, and there is an increasing interest in stress reduction and relaxation effects in modern society.

On the other hand, since palatability for a scent varies depending on a person, it is desired that the scent is easily accepted by many people while having a desired effect. For example, in Patent Literature 1, it is proposed a fragrance composition that is a scent having good palatability and easily accepted, and has a relaxing effect.

CITATION LIST

Patent Literature

Patent Literature 1: JP 2008-101129 A

SUMMARY OF INVENTION

Technical Problem

Nevertheless, in a conventional fragrance or flavor composition, in addition to a specific major compound as an active ingredient, many other ingredients are blended. For example, in the fragrance composition, as is described in Patent Literature 1, an essential oil of *Helichrysum stoechas* extracted from that neutral fraction with an acidic and alkaline aqueous solution is an active blend of as many as 60 kinds of ingredients.

Considering the above situation, an object of the present invention is to provide a novel odorant composition consisting of a small number of chemical compounds, which has good palatability allowing peoples to feel comfortable.

Solution to Problem

The present inventors have focused on chemical compounds of aldehydes and ketones, based on various data of chemical analyses and sensory evaluation for the effective odorant composition and blending ratios of compounds. As a result, the present inventors have found that an odorant composition that is easily and universally accepted and allows a person to feel comfortable can be prepared with 15 or a smaller number of compounds out of predetermined compounds blended at appropriate ratios. As a result of additional studies, the present inventors have further revealed that 25 or a smaller number of compounds, which may include optional odorant ingredients, can be formulated, and have completed the present invention.

The present invention includes the following aspects.

[1] An odorant composition consisting of: when the total mass of ingredients contained in the odorant composition is 100.0% by mass,
40.0% by mass or more and 97.5% by mass or less of an ingredient (A) composed of aldehydes;
1.0% by mass or more and 20.0% by mass or less of an ingredient (B) composed of a ketone(s); and
the balance being an ingredient (C) composed of a chemical compound(s) other than the ingredient (A) and the ingredient (B), in which
the aldehydes of the ingredient (A) are:
an essential ingredient (A1) composed of nonanal; and
an optional ingredient (A2) selected from the group consisting of decanal, heptanal, octanal, benzaldehyde, undecanal, hexanal, and combinations thereof,
the ketone(s) of the ingredient (B) is selected from the group consisting of 6-methyl-5-hepten-2-one, cyclohexanone, 1-phenylethanone, 2-decanone, 2-undecanone, and combinations thereof, and
the compound(s) of the ingredient (C) is selected from the group consisting of limonene, 1,8-cineole, menthol, 1-octanol, 3-hexyn-1-ol, 2-nonen-1-ol, dodecane, hexanoic acid, octanoic acid, nonanoic acid, 2(5H)-furanone, p-cymene, sotolon, and combinations thereof.

[2] The odorant composition according to [1], in which
the content of the ingredient (A) is more than 55.0% by mass and 95.0% by mass or less, and
the content of the essential ingredient (A1) is 27.0% by mass or more and 64.0% by mass or less.

[3] The odorant composition according to [2], in which
the ingredient (B) is selected from the group consisting of 6-methyl-5-hepten-2-one, 1-phenylethanone, 2-decanone, 2-undecanone, and combinations thereof, and
the ingredient (C) is selected from the group consisting of limonene, 1,8-cineole, menthol, 2-nonen-1-ol, hexanoic acid, octanoic acid, nonanoic acid, p-cymene, and combinations thereof.

[4] The odorant composition according to [3], in which
the content of the ingredient (A) is 75.0% by mass or more and 95.0% by mass or less,
the content of the essential ingredient (A1) is 43.0% by mass or more and 62.0% by mass or less, and
a content of the ingredient (B) is 1.0% by mass or more and 12.0% by mass or less.

[5] The odorant composition according to [4], in which
the content of the ingredient (A) is 75.0% by mass or more and 80.0% by mass or less,
the content of the essential ingredient (A1) is 48.0% by mass or more and 55.0% by mass or less,
the content of the ingredient (B) is 8.0% by mass or more and 11.0% by mass or less,
the ingredient (B) is 6-methyl-5-hepten-2-one or a combination of 6-methyl-5-hepten-2-one, 1-phenylethanone, and 2-decanone, and
the ingredient (C) is a combination of limonene, 1,8-cineole, and menthol, a combination of limonene, 1,8-cineole, menthol, and p-cymene, or a combination of limonene, 1,8-cineole, menthol, 2-nonen-1-ol, and p-cymene.

[6] The odorant composition according to [4], in which
the content of the ingredient (A) is 81.0% by mass or more and 85.0% by mass or less,
the content of the essential ingredient (A1) is 58.0% by mass or more and 62.0% by mass or less,
the content of the ingredient (B) is 8.0% by mass or more and 10.0% by mass or less,
the ingredient (B) is a combination of 6-methyl-5-hepten-2-one and 1-phenylethanone or a combination of 6-methyl-5-hepten-2-one, 1-phenylethanone, and 2-decanone, and
the ingredient (C) is a combination of limonene and menthol, a combination of limonene, 1,8-cineole, and menthol, or a combination of limonene, 1,8-cineole, menthol, 2-nonen-1-ol, and nonanoic acid.

[7] The odorant composition according to [4], in which the content of the ingredient (A) is 81.0% by mass or more and 85.0% by mass or less,
the content of the essential ingredient (A1) is 58.0% by mass or more and 62.0% by mass or less,
the content of the ingredient (B) is 2.0% by mass or more and 5.0% by mass or less,
the ingredient (B) is 6-methyl-5-hepten-2-one, a combination of 6-methyl-5-hepten-2-one and 1-phenylethanone, or a combination of 6-methyl-5-hepten-2-one, 1-phenylethanone, 2-decanone, and 2-undecanone, and
the ingredient (C) is a combination of limonene, menthol, and 2-nonen-1-ol or a combination of limonene, 1,8-cineole, menthol, 2-nonen-1-ol, and p-cymene.

[8] A product containing the odorant composition according to any one of [1] to [7], the product being selected from the group consisting of perfumery and cosmetics, food and drink, and a tobacco product.

[9] A microcapsule or a nanocapsule containing the odorant composition according to any one of [1] to [7].

[10] An ink containing the microcapsule or the nanocapsule according to [9].

[11] A printed matter using the ink according to [10].

[12] A drawing material containing the microcapsule or the nanocapsule according to [9].

[13] A material using the odorant composition according to any one of [1] to [7].

[14] The material according to [13], which is paper, a fabric, a woven fabric, a knitted fabric, a nonwoven fabric, a rug, a plate material, an ornament, a wrapping and packaging material, or a toy.

Advantageous Effects of Invention

The odorant composition of the present invention is prepared using a smaller number of chemical compounds than a conventional odorant composition, and still preserved good palatability allowing peoples to feel comfortable. In addition, the odorant composition of the present invention can enhance a positive emotion of a person who has smelled a scent of the odorant composition. The odorant composition of the present invention can be blended in perfumery and cosmetics, food and drink, a tobacco product, an ink, a drawing material, and the like, can be used for various materials such as a wrapping and packaging material and a toy, and can enhance commercial values thereof.

DESCRIPTION OF EMBODIMENTS

Figure 1:
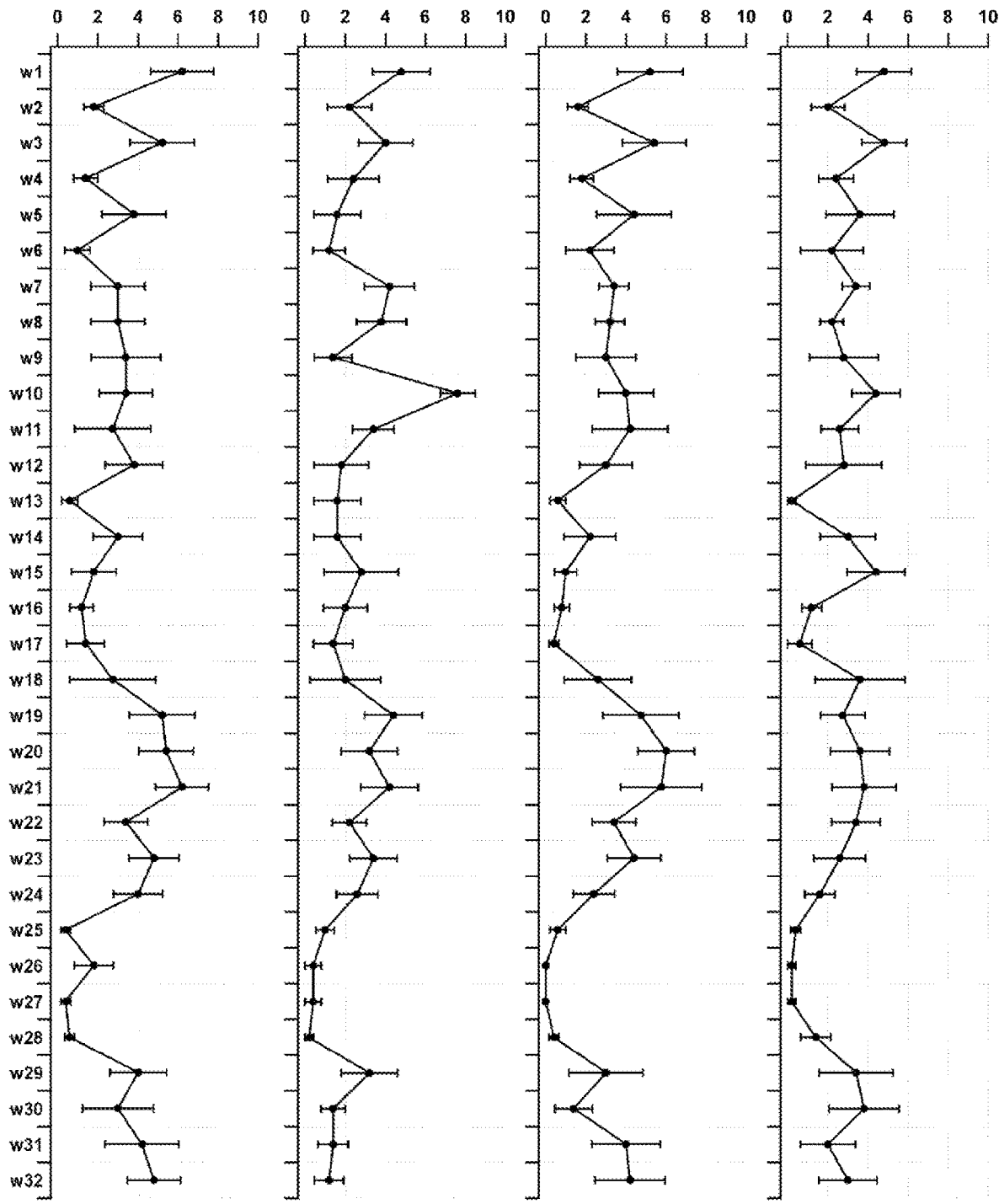
FIG. 1 is a graph showing results of sensory evaluation 1 of scents of odorant compositions of Examples 1 to 4.

Hereinafter, embodiments of the present invention will be described in detail. Note that a specific form is not limited to the following embodiments, and changes in design and the like without departing from the gist of the present invention are also included in the present invention.

An odorant composition of the present invention contains, as main ingredients, an ingredient (A) composed of aldehydes and an ingredient (B) composed of a ketone(s). That is, in the odorant composition of the present invention, when the total mass of ingredients contained in the odorant composition is 100.0% by mass, a total blending ratio of the ingredient (A) and the ingredient (B) is more than 50.0% by mass, preferably 53.0% by mass or more, more preferably 55.0% by mass or more, still more preferably 70.0% by mass or more, and further still more preferably 80.0% by mass or more. An upper limit value of the total blending ratio of the ingredient (A) and the ingredient (B) is not particularly limited, but is preferably 97.5% by mass or less, and more preferably 95.5% by mass or less.

[Ingredient (A)]

In the odorant composition of the present invention, when the total mass of ingredients contained in the odorant composition is 100.0% by mass, a blending ratio of the ingredient (A) is 40.0% by mass or more and 90.0% by mass or less.

Examples of the aldehyde of the ingredient (A) include propanal, 2-methylpropanal, 2-ethylpropanal, butanal, 2-methylbutanal, 2-ethylbutanal, 2-butenal, hexanal, 2-methylhexanal, 2-ethylhexanal, octanal, 2-methyloctanal, 2-ethyloctanal, heptanal, 2-methylheptanal, 2-ethylheptanal, 4-heptenal, 2,4-octadienal, nonanal, 2-methylnonanal, 2-nonenal, 2,4-nonadienal, 2,6-nonadienal, decanal, 2,4-decadienal, undecanal, 10-undecenal, 2,4-undecadienal, dodecanal, citronellal, citral, hydroxycitronellal, benzaldehyde, cinnamyl aldehyde, α-amyl cinnamyl aldehyde, phenylacetaldehyde, vanillin, ethyl vanillin, furfural, and heliotropin.

In a preferred embodiment, the aldehydes of the ingredient (A) are the essential ingredient (A1) composed of nonanal and the optional ingredient (A2) selected from the group consisting of decanal, heptanal, octanal, benzaldehyde, undecanal, hexanal, and combinations thereof.

When the blending ratio of the ingredient (A) is within the above range and the above-described chemical compounds are used as the aldehydes, it is possible to obtain an odorant composition in which the ingredient (B) and an ingredient (C) described later are blended and which has good scent palatability allowing peoples to feel comfortable.

Aldehydes blending ratios of the essential ingredient (A1) and the optional ingredient (A2) in the ingredient (A) are appropriately adjusted such that the blending ratio of the whole ingredient (A) in the odorant composition satisfies the above range.

First Embodiment

In a first embodiment of the present invention, when the total mass of ingredients contained in the odorant composition is 100.0% by mass,
- as the content of the essential ingredient (A1) of the ingredient (A),
- nonanal is contained in an amount of 30.0% by mass or more and 55.0% by mass or less,
- the aldehyde of the optional ingredient (A2) of the ingredient (A) is a combination of decanal, heptanal, and octanal, a combination of decanal, heptanal, and benzaldehyde, a combination of decanal, heptanal, and undecanal, a combination of decanal, heptanal, octanal, and benzaldehyde, or a combination of decanal, heptanal, benzaldehyde, and undecanal, and
- as the content of the optional ingredient (A2),
- decanal is contained in an amount of 4.0% by mass or more and 24.0% by mass or less,
- heptanal is contained in an amount of 2.0% by mass or more and 30.0% by mass or less,
- octanal is contained in an amount of 1.0% by mass or more and 15.0% by mass or less,
- benzaldehyde is contained in an amount of 1.0% by mass or more and 10.0% by mass or less, and
- undecanal is contained in an amount of 0.5% by mass or more and 12.0% by mass or less.

In a preferred embodiment, when the total mass of ingredients contained in the odorant composition is 100.0% by mass,
- as the content of the essential ingredient (A1) of the ingredient (A),
- nonanal is contained in an amount of 33.0% by mass or more and 52.0% by mass or less, and
- as the content of the optional ingredient (A2) of the ingredient (A),
- decanal is contained in an amount of 12.0% by mass or more and 24.0% by mass or less,
- heptanal is contained in an amount of 2.0% by mass or more and 30.0% by mass or less,
- octanal is contained in an amount of 2.0% by mass or more and 13.0% by mass or less,
- benzaldehyde is contained in an amount of 1.0% by mass or more and 7.0% by mass or less, and
- undecanal is contained in an amount of 0.5% by mass or more and 12.0% by mass or less.

In a more preferred embodiment, when the total mass of ingredients contained in the odorant composition is 100.0% by mass,
- as the content of the essential ingredient (A1) of the ingredient (A),
- nonanal is contained in an amount of 34.0% by mass or more and 52.0% by mass or less, and
- as the content of the optional ingredient (A2) of the ingredient (A),
- decanal is contained in an amount of 12.0% by mass or more and 24.0% by mass or less,
- heptanal is contained in an amount of 2.0% by mass or more and 30.0% by mass or less,
- octanal is contained in an amount of 2.0% by mass or more and 13.0% by mass or less,
- benzaldehyde is contained in an amount of 1.0% by mass or more and 7.0% by mass or less, and
- undecanal is contained in an amount of 9.0% by mass or more and 12.0% by mass or less.

In a still more preferred embodiment, when the total mass of ingredients contained in the odorant composition is 100.0% by mass,
- as the content of the essential ingredient (A1) of the ingredient (A),
- nonanal is contained in an amount of 35.0% by mass or more and 52.0% by mass or less, and
- as the content of the optional ingredient (A2) of the ingredient (A),
- decanal is contained in an amount of 13.0% by mass or more and 24.0% by mass or less,
- heptanal is contained in an amount of 2.0% by mass or more and 30.0% by mass or less,
- octanal is contained in an amount of 5.0% by mass or more and 13.0% by mass or less,
- benzaldehyde is contained in an amount of 1.0% by mass or more and 6.0% by mass or less, and
- undecanal is contained in an amount of 9.0% by mass or more and 11.0% by mass or less.

In a further still more preferred embodiment, when the total mass of ingredients contained in the odorant composition is 100.0% by mass,
- as the content of the essential ingredient (A1) of the ingredient (A),
- nonanal is contained in an amount of 40.0% by mass or more and 52.0% by mass or less,
- the aldehyde of the optional ingredient (A2) of the ingredient (A) is a combination of decanal, heptanal, octanal, and benzaldehyde, and
- as the content of the optional ingredient (A2),
- decanal is contained in an amount of 12.0% by mass or more and 18.0% by mass or less, p heptanal is contained in an amount of 3.0% by mass or more and 8.0% by mass or less,
- octanal is contained in an amount of 8.0% by mass or more and 13.0% by mass or less, and
- benzaldehyde is contained in an amount of 3.0% by mass or more and 6.0% by mass or less.

In a further still more preferred embodiment, when the total mass of ingredients contained in the odorant composition is 100.0% by mass,
- as the content of the essential ingredient (A1) of the ingredient (A),
- nonanal is contained in an amount of 43.0% by mass or more and 46.0% by mass or less, and
- as the content of the optional ingredient (A2) of the ingredient (A),
- decanal is contained in an amount of 13.0% by mass or more and 15.0% by mass or less,
- heptanal is contained in an amount of 3.0% by mass or more and 5.0% by mass or less,
- octanal is contained in an amount of 8.0% by mass or more and 10.0% by mass or less, and
- benzaldehyde is contained in an amount of 3.0% by mass or more and 5.0% by mass or less.

Second Embodiment

In a second embodiment of the present invention, when the total mass of ingredients contained in the odorant composition is 100.0% by mass, the content of the ingredient (A) is more than 55.0% by mass and 95.0% by mass or less, and the content of the essential ingredient (A1) is 27.0% by mass or more and 64.0% by mass or less.

In a preferred embodiment, when the total mass of ingredients contained in the odorant composition is 100.0% by mass, the content of the ingredient (A) is more than 75.0% by mass and 95.0% by mass or less, and the content of the essential ingredient (A1) is 43.0% by mass or more and 62.0% by mass or less.

In an aspect of the preferred embodiment, when the total mass of ingredients contained in the odorant composition is 100.0% by mass, the content of the ingredient (A) is more than 75.0% by mass and 80.0% by mass or less, and the content of the essential ingredient (A1) is 48.0% by mass or more and 55.0% by mass or less.

In another aspect of the preferred embodiment, when the total mass of ingredients contained in the odorant composition is 100.0% by mass, the content of the ingredient (A) is 81.0% by mass or more and 85.0% by mass or less, and the content of the essential ingredient (A1) is 58.0% by mass or more and 62.0% by mass or less.

In still another aspect of the preferred embodiment, when the total mass of ingredients contained in the odorant composition is 100.0% by mass, the content of the ingredient (A) is 81.0% by mass or more and 85.0% by mass or less, and the content of the essential ingredient (A1) is 58.0% by mass or more and 62.0% by mass or less.

In further still another aspect of the preferred embodiment, when the total mass of ingredients contained in the odorant composition is 100.0% by mass, the content of the ingredient (A) is 80.0% by mass or more and 85.0% by mass or less, and the content of the essential ingredient (A1) is 52.0% by mass or more and 57.0% by mass or less.

In further still another aspect of the preferred embodiment, when the total mass of ingredients contained in the odorant composition is 100.0% by mass, the content of the ingredient (A) is 83.0% by mass or more and 87.0% by mass or less, and the content of the essential ingredient (A1) is 56.0% by mass or more and 59.0% by mass or less.

[Ingredient (B)]

In the odorant composition of the present invention, when the total mass of ingredients contained in the odorant composition is 100.0% by mass, a blending ratio of the ingredient (B) is 1.0% by mass or more and 20.0% by mass or less.

Examples of the ketone of the ingredient (B) include an aliphatic ketone, a cyclic ketone, and an aromatic ketone. These ketones may be used singly or in combination of two or more kinds thereof.

Examples of the aliphatic ketone include 2-hexanone, 2-methyl-3-hexanone, 5-methyl-2-hexanone, 2-heptanone, 3-heptanone, 4-heptanone, 2-methyl-3-heptanone, 5-methyl-3-heptanone, 2,6-dimethyl-4-heptanone, 6-methyl-5-hepten-2-one, 2-octanone, 3-octanone, 1-octen-3-one, 2-nonanone, 5-nonanone, 8-nonen-2-one, 2-decanone, 2-undecanone, 2-tridecanone, 2,3-heptanedione, 2,4-heptanedione, 2,5-heptanedione, 2,6-heptanedione, 3,4-heptanedione, and 3,5-heptanedione.

Examples of the cyclic ketone include menthone, isomentone, carvone, dihydrocarvone, pulegone, piperiton, 1-acetyl-3,3-dimethyl-1-cyclohexene, cis-jasmon, α-ilon, β-ilon, γ-ilon, homofuronol, maltol, ethyl maltol, cyclotene, 3,4-dimethyl-1,2-cyclopentadione, sotolon, α-damascone, β-damascone, γ-damascone, δ-damascone, α-damasenone, β-damasenone, γ-damasenone, nootkatone, dihydronootkatone, ethyl maltol, cyclohexanone, 2-sec-butylcyclohexanone, α-ionone, β-ionone, γ-ionone, α-methylionone, β-methylionone, γ-methylionone, α-isomethylionone, β-isomethylionone, γ-isomethylionone, furaneol, and camphor.

Examples of the aromatic ketone include acetonaphthone, 1-phenylethanone (acetophenone), anisylideneacetone, raspberry ketone, p-methylacetophenone, anisylacetone, and p-methoxyacetophenone.

Here, among the chemical compounds of the ingredient (B) exemplified above, sotolon has extremely strong aroma, and has an odor threshold of 0.001 ppb (in water), which is considered to be the smallest value among currently known chemical compounds. Therefore, it is not appropriate to blend 1.0% by mass or more of sotolon alone in the odorant composition of the present invention. In addition, when sotolon is blended in combination with another chemical compound, a blending ratio of sotolon is limited to a very small value, and is specifically preferably $3 \times 10^{-8}$% by mass or less. In other words, with this blending ratio, sotolon is favorably combined with other chemical compounds contained in the odorant composition of the present invention, and can further enhance the effect of the present invention. For this reason, sotolon is classified into a ketone in terms of chemical structure, but in the odorant composition of the present invention, sotolon is handled as a chemical compound of the ingredient (C) described later.

In a preferred embodiment, the ketone of the ingredient (B) is selected from the group consisting of 6-methyl-5-hepten-2-one, cyclohexanone, 1-phenylethanone, 2-decanone, 2-undecanone, and combinations thereof.

When the blending ratio of the ingredient (B) is within the above range and the above-described chemical compound is used as the ketone, it is possible to obtain an odorant composition in which the ingredient (A) and the ingredient (C) described later are blended and which has good scent palatability allowing peoples to feel comfortable.

First Embodiment

In the first embodiment of the present invention, when the total mass of ingredients contained in the odorant composition is 100.0% by mass, the content of the ingredient (B) is preferably 3.0% by mass or more and 13.0% by mass or less, and more preferably 5.0% by mass or more and 13.0% by mass or less.

In a preferred embodiment, the ketone of the ingredient (B) is 6-methyl-5-hepten-2-one, a combination of 6-methyl-5-hepten-2-one and 1-phenylethanone, or a combination of 6-methyl-5-hepten-2-one and 2-decanone, and when the total mass of ingredients contained in the odorant composition is 100.0% by mass, as the content of the ingredient (B), 6-methyl-5-hepten-2-one is contained in an amount of 4.0% by mass or more and 11.0% by mass or less, 1-phenylethanone is contained in an amount of 0.5% by mass or more and 4.0% by mass or less, and 2-decanone is contained in an amount of 1.0% by mass or more and 2.0% by mass or less.

In a more preferred embodiment, when the total mass of ingredients contained in the odorant composition is 100.0% by mass, the content of the ingredient (B) is 5.0% by mass or more and 11.0% by mass or less.
and
the ketone of the ingredient (B) is a combination of 6-methyl-5-hepten-2-one and 1-phenylethanone or a combination of 6-methyl-5-hepten-2-one and 2-decanone, and
as the content of the ingredient (B),
6-methyl-5-hepten-2-one is contained in an amount of 4.0% by mass or more and 11.0% by mass or less,
1-phenylethanone is contained in an amount of 1.0% by mass or more and 4.0% by mass or less, and
2-decanone is contained in an amount of 1.0% by mass or more and 2.0% by mass or less.

In a still more preferred embodiment, when the total mass of ingredients contained in the odorant composition is 100.0% by mass,
the ketone of the ingredient (B) is 6-methyl-5-hepten-2-one, and
as the content of the ingredient (B),
6-methyl-5-hepten-2-one is contained in an amount of 6.0% by mass or more and 11.0% by mass or less.

In a further still more preferred embodiment, when the total mass of ingredients contained in the odorant composition is 100.0% by mass,
the ketone of the ingredient (B) is 6-methyl-5-hepten-2-one, and
as the content of the ingredient (B),
6-methyl-5-hepten-2-one is contained in an amount of 8.0% by mass or more and 10.0% by mass or less.

Second Embodiment

In the second embodiment of the present invention, the ketone of the ingredient (B) is selected from the group consisting of 6-methyl-5-hepten-2-one, 1-phenylethanone, 2-decanone, 2-undecanone, and combinations thereof.

In a preferred embodiment, when the total mass of ingredients contained in the odorant composition is 100.0% by mass, the content of the ingredient (B) is 1.0% by mass or more and 12.0% by mass or less.

In an aspect of the preferred embodiment, when the total mass of ingredients contained in the odorant composition is 100.0% by mass, the content of the ingredient (B) is 8.0% by mass or more and 11.0% by mass or less, and
the ingredient (B) is 6-methyl-5-hepten-2-one or a combination of 6-methyl-5-hepten-2-one, 1-phenylethanone, and 2-decanone.

In another aspect of the preferred embodiment, when the total mass of ingredients contained in the odorant composition is 100.0% by mass, the content of the ingredient (B) is 8.0% by mass or more and 10.0% by mass or less, and
the ingredient (B) is a combination of 6-methyl-5-hepten-2-one and 1-phenylethanone or a combination of 6-methyl-5-hepten-2-one, 1-phenylethanone, and 2-decanone.

In still another aspect of the preferred embodiment, when the total mass of ingredients contained in the odorant composition is 100.0% by mass, the content of the ingredient (B) is 2.0% by mass or more and 5.0% by mass or less, and
the ingredient (B) is 6-methyl-5-hepten-2-one, a combination of 6-methyl-5-hepten-2-one and 1-phenylethanone, or a combination of 6-methyl-5-hepten-2-one, 1-phenylethanone, 2-decanone, and 2-undecanone.

In further still another aspect of the preferred embodiment, when the total mass of ingredients contained in the odorant composition is 100.0% by mass, the content of the ingredient (B) is 4.0% by mass or more and 9.0% by mass or less, and
the ingredient (B) is a combination of 6-methyl-5-hepten-2-one, 1-phenylethanone, 2-decanone, and 2-undecanone.

In further still another aspect of the preferred embodiment, when the total mass of ingredients contained in the odorant composition is 100.0% by mass, the content of the ingredient (B) is 1.0% by mass or more and 3.5% by mass or less, and
the ingredient (B) is 6-methyl-5-hepten-2-one or a combination of 6-methyl-5-hepten-2-one, 2-decanone, and 2-undecanone.

[Ingredient (C)]

The odorant composition of the present invention contains the ingredient (C) composed of a chemical compound(s) other than the ingredient (A) and the ingredient (B). When the total mass of ingredients contained in the odorant composition is 100.0% by mass, a blending ratio of the ingredient (C) is the balance excluding the total blending ratio of the ingredient (A) and the ingredient (B).

In the odorant composition of the present invention, the chemical compound of the ingredient (C) is selected from the group consisting of limonene, 1,8-cineole, menthol, 1-octanol, 3-hexyn-1-ol, 2-nonen-1-ol, dodecane, hexanoic acid, octanoic acid, nonanoic acid, 2(5H)-furanone, p-cymene, sotolon, and combinations thereof.

By combining these chemical compounds with the ingredient (A) and the ingredient (B), it is possible to obtain an odorant composition having good scent palatability allowing peoples to feel comfortable.

First Embodiment

In the first embodiment of the present invention, the chemical compound of the ingredient (C) is selected from the group consisting of limonene, 1,8-cineole, menthol, nonanoic acid, 2(5H)-furanone, p-cymene, sotolon, and combinations thereof. In this case, preferred embodiments of the chemical compound and a blending ratio thereof are exemplified as follows.

(1) As the chemical compound of the ingredient (C), limonene is used, and when the total mass of ingredients contained in the odorant composition is 100.0% by mass, a blending ratio of limonene is 2.0% by mass or more and 16.0% by mass or less.

(2) As the chemical compound of the ingredient (C), limonene and 1,8-cineole are used, and when the total mass of ingredients contained in the odorant composition is 100.0% by mass, a blending ratio of limonene is 2.0% by mass or more and 6.0% by mass or less, and a blending ratio of 1,8-cineole is 2.0% by mass or more and 10.0% by mass or less.

(3) As the chemical compound of the ingredient (C), limonene and menthol are used, and when the total mass of ingredients contained in the odorant composition is 100.0% by mass, a blending ratio of limonene is 2.0% by mass or more and 6.0% by mass or less, and a blending ratio of menthol is 2.0% by mass or more and 5.0% by mass or less.

(4) As the chemical compound of the ingredient (C), menthol and 1,8-cineole are used, and when the total mass of ingredients contained in the odorant composition is 100.0% by mass, a blending ratio of menthol is 2.0% by mass or more and 5.0% by mass or less, and a blending ratio of 1,8-cineole is 2.0% by mass or more and 10.0% by mass or less.

(5) As the chemical compound of the ingredient (C), limonene, menthol, and nonanoic acid are used, and when the total mass of ingredients contained in the odorant composition is 100.0% by mass, a blending ratio of limonene is 1.0% by mass or more and 3.0% by mass or less, a blending ratio of menthol is 5.0% by mass or more and 7.0% by mass or less, and a blending ratio of nonanoic acid is 3.0% by mass or more and 5.0% by mass or less.

(6) As the chemical compound of the ingredient (C), limonene, 1,8-cineole, menthol, and nonanoic acid are used, and when the total mass of ingredients contained in the odorant composition is 100.0% by mass, a blending ratio of limonene is 1.0% by mass or more and 3.0% by mass or less, a blending ratio of 1,8-cineole is 1.0% by mass or more and 2.0% by mass or less, a blending ratio of menthol is 5.0% by mass or more and 7.0% by mass or less, and a blending ratio of nonanoic acid is 3.0% by mass or more and 5.0% by mass or less.

(7) As the chemical compound of the ingredient (C), menthol and p-cymene are used, and when the total mass of ingredients contained in the odorant composition is 100.0% by mass, a blending ratio of menthol is 16.0% by mass or more and 18.0% by mass or less, and a blending ratio of p-cymene is 1.0% by mass or more and 2.0% by mass or less.

(8) As the chemical compound of the ingredient (C), menthol, nonanoic acid, and p-cymene are used, and when the total mass of ingredients contained in the odorant composition is 100.0% by mass, a blending ratio of menthol is 17.0% by mass or more and 19.0% by mass or less, a blending ratio of nonanoic acid is 0.5% by mass or more and 1.5% by mass or less, and a blending ratio of p-cymene is 1.0% by mass or more and 2.0% by mass or less.

(9) As the chemical compound of the ingredient (C), menthol, nonanoic acid, and 2(5H)-furanone are used, and when the total mass of ingredients contained in the odorant composition is 100.0% by mass, a blending ratio of menthol is 4.0% by mass or more and 6.0% by mass or less, a blending ratio of nonanoic acid is 10.5% by mass or more and 12.5% by mass or less, and a blending ratio of 2(5H)-furanone is 3.0% by mass or more and 5.0% by mass or less.

(10) As the chemical compound of the ingredient (C), 2(5H)-furanone is used, and when the total mass of ingredients contained in the odorant composition is 100.0% by mass, a blending ratio of 2(5H)-furanone is 4.0% by mass or more and 6.0% by mass or less.

Note that in the above embodiments (1) to (10), sotolon may be further blended. When sotolon is blended, a blending ratio of sotolon is $3 \times 10^{-8}$% by mass or less.

Second Embodiment

In the second embodiment of the present invention, the chemical compound of the ingredient (C) is selected from the group consisting of limonene, 1,8-cineole, menthol, 2-nonen-1-ol, hexanoic acid, octanoic acid, nonanoic acid, p-cymene, sotolon, and combinations thereof.

In an aspect of the present embodiment, the chemical compound of the ingredient (C) is a combination of limonene, 1,8-cineole, and menthol, a combination of limonene, 1,8-cineole, menthol, and p-cymene, or a combination of limonene, 1,8-cineole, menthol, 2-nonen-1-ol, and p-cymene.

In another aspect of the present embodiment, the chemical compound of the ingredient (C) is a combination of limonene and menthol, a combination of limonene, 1,8-cineole, and menthol, or a combination of limonene, 1,8-cineole, menthol, 2-nonen-1-ol, and nonanoic acid.

In still another aspect of the present embodiment, the chemical compound of the ingredient (C) is a combination of limonene, menthol, and 2-nonen-1-ol or a combination of limonene, 1,8-cineole, menthol, 2-nonen-1-ol, and p-cymene.

In further still another aspect of the present embodiment, the chemical compound of the ingredient (C) is a combination of limonene, menthol, and 2-nonen-1-ol or a combination of limonene, menthol, 2-nonen-1-ol, and p-cymene.

In further still another aspect of the present embodiment, the chemical compound of the ingredient (C) is a combination of limonene, menthol, and 2-nonen-1-ol or a combination of limonene, menthol, 2-nonen-1-ol, nonanoic acid, and p-cymene.

Note that in the above aspects, sotolon may be further blended. When sotolon is blended, a blending ratio of sotolon is $3 \times 10^{-8}$% by mass or less.

Based on the above, preferable forms of formulation of the odorant composition of the present invention are exemplified in Tables 1 to 11, 12-1, 12-2, 13-1, 13-2, 14-1, and 14-2 below separately for the first embodiment and the second embodiment described above. Note that a blending ratio (% by mass) of each chemical compound in Tables is a value when the total mass of ingredients contained in the odorant composition is 100.0% by mass.

First Embodiment

Formulation with Eight Compounds

TABLE 1

| Ingredient | Chemical Compound | Formulation 1 | Formulation 2 | Formulation 3 | Formulation 4 |
|---|---|---|---|---|---|
| A | Nonanal | 45.40 | 50.10 | 42.41 | 51.20 |
|  | Decanal | 14.30 | 15.40 | 16.61 | 13.30 |
|  | Heptanal | 4.00 | 6.40 | 6.32 | 7.70 |
|  | Octanal | 8.60 | 11.20 | 11.92 | 9.90 |
|  | Benzaldehyde | 3.50 | 4.00 | 5.62 | 4.00 |
| B | 6-Methyl-5-hepten-2-one | 9.30 | 6.80 | 10.52 | 10.40 |
|  | 1-Phenylethanone | 0.00 | 0.00 | 0.00 | 0.90 |
| C | Limonene | 5.10 | 3.10 | 3.00 | 0.00 |
|  | 1,8-Cineole | 9.80 | 3.00 | 0.00 | 0.00 |
|  | Menthol | 0.00 | 0.00 | 3.60 | 2.60 |
|  | Total | 100.0 | 100.0 | 100.0 | 100.0 |

(Unit: % by mass)

TABLE 2

| Ingredient | Chemical Compound | Formulation 5 | Formulation 6 | Formulation 7 | Formulation 8 |
|---|---|---|---|---|---|
| A | Nonanal | 36.28 | 47.08 | 49.84 | 41.60 |
|  | Decanal | 14.95 | 19.63 | 22.66 | 17.99 |
|  | Heptanal | 28.67 | 9.20 | 2.97 | 5.07 |
|  | Octanal | 0.00 | 0.00 | 6.01 | 0.00 |
|  | Benzaldehyde | 2.49 | 0.00 | 0.00 | 1.58 |
|  | Undecanal | 0.00 | 0.00 | 0.00 | 10.60 |
| B | 6-Methyl-5-hepten-2-one | 7.89 | 9.69 | 8.08 | 4.56 |
|  | 1-Phenylethanone | 0.00 | 1.82 | 2.44 | 0.00 |
|  | 2-Decanone | 0.00 | 0.00 | 0.00 | 1.14 |
| C | Limonene | 2.69 | 1.94 | 2.20 | 0.00 |
|  | 1,8-Cineole | 3.77 | 0.00 | 0.00 | 0.00 |
|  | Menthol | 3.26 | 6.69 | 5.80 | 17.46 |
|  | Nonanoic acid | 0.00 | 3.95 | 0.00 | 0.00 |
|  | Total | 100.0 | 100.0 | 100.0 | 100.0 |

(Unit: % by mass)

TABLE 3

| Ingredient | Chemical Compound | Formulation 9 | Formulation 10 | Formulation 11 | Formulation 12 |
|---|---|---|---|---|---|
| A | Nonanal | 43.0-46.0 | 48.0-51.0 | 41.0-43.0 | 41.0-51.0 |
|  | Decanal | 13.0-15.0 | 14.0-16.0 | 16.0-17.0 | 13.0-17.0 |
|  | Heptanal | 3.0-5.0 | 6.0-7.0 | 6.0-7.0 | 3.0-7.0 |
|  | Octanal | 8.0-10.0 | 10.0-12.0 | 11.0-13.0 | 8.0-13.0 |
|  | Benzaldehyde | 3.0-5.0 | 3.0-5.0 | 5.0-6.0 | 3.0-6.0 |
| B | 6-Methyl-5-hepten-2-one | 8.0-10.0 | 6.0-8.0 | 10.0-11.0 | 6.0-11.0 |
| C | Limonene | 4.0-6.0 | 2.0-4.0 | 2.0-4.0 | 2.0-6.0 |
|  | 1,8-Cineole | 9.0-10.0 | 2.0-4.0 | — | 2.0-10.0* |
|  | Menthol | — | — | 3.0-4.0 | 3.0-4.0* |
|  | Total | (The total mass is adjusted to be 100.0% by mass.) | | | |

(Unit: % by mass)
*In Formulation 12, either one of 1,8-cineole and menthol is blended.

TABLE 4

| Ingredient | Chemical Compound | Formulation 13 | Formulation 14 | Formulation 15 | Formulation 16 |
|---|---|---|---|---|---|
| A | Nonanal | 35.0-38.0 | 46.0-48.0 | 48.0-51.0 | 40.0-43.0 |
|  | Decanal | 14.0-17.0 | 19.0-20.0 | 21.0-24.0 | 16.0-19.0 |
|  | Heptanal | 28.0-30.0 | 8.0-10.0 | 2.0-4.0 | 4.0-6.0 |
|  | Octanal | — | — | 5.0-7.0 | — |
|  | Benzaldehyde | 2.0-4.0 | — | — | 1.0-2.0 |
|  | Undecanal | — | — | — | 9.0-11.0 |
| B | 6-Methyl-5-hepten-2-one | 7.0-9.0 | 8.0-10.0 | 7.0-9.0 | 4.0-6.0 |
|  | 1-Phenylethanone | — | 1.0-2.0 | 2.0-4.0 | — |
|  | 2-Decanone | — | — | — | 1.0-2.0 |
| C | Limonene | 2.0-4.0 | 1.0-3.0 | 2.0-3.0 | — |
|  | 1,8-Cineole | 3.0-5.0 | — | — | — |
|  | Menthol | 3.0-5.0 | 6.0-8.0 | 5.0-7.0 | 16.0-18.0 |
|  | Nonanoic acid | — | 3.0-5.0 | — | — |
|  | Total | (The total mass is adjusted to be 100.0% by mass.) | | | |

(Unit: % by mass)

Formulation with Nine Compounds

TABLE 5

| Ingredient | Chemical Compound | Formulation 17 | Formulation 18 | Formulation 19 | Formulation 20 |
|---|---|---|---|---|---|
| A | Nonanal | 35.43 | 46.43 | 48.80 | 41.17 |
|  | Decanal | 14.59 | 19.36 | 22.19 | 17.80 |
|  | Heptanal | 27.99 | 9.07 | 2.91 | 5.02 |
|  | Octanal | 2.34 | 0.00 | 5.89 | 0.00 |
|  | Benzaldehyde | 2.43 | 0.00 | 2.08 | 1.56 |
|  | Undecanal | 0.00 | 0.00 | 0.00 | 10.50 |

TABLE 5-continued

| Ingredient | Chemical Compound | Formulation 17 | Formulation 18 | Formulation 19 | Formulation 20 |
|---|---|---|---|---|---|
| B | 6-Methyl-5-hepten-2-one | 7.71 | 9.56 | 7.91 | 4.51 |
|  | 1-Phenylethanone | 0.00 | 1.79 | 2.39 | 0.00 |
|  | 2-Decanone | 0.00 | 0.00 | 0.00 | 1.14 |
| C | Limonene | 2.63 | 1.92 | 2.15 | 0.00 |
|  | 1,8-Cineole | 3.69 | 1.38 | 0.00 | 0.00 |
|  | Menthol | 3.19 | 6.60 | 5.68 | 17.28 |
|  | Nonanoic acid | 0.00 | 3.89 | 0.00 | 0.00 |
|  | p-Cymene | 0.00 | 0.00 | 0.00 | 1.02 |
|  | Total | 100.0 | 100.0 | 100.0 | 100.0 |

(Unit: % by mass)

TABLE 6

| Ingredient | Chemical Compound | Formulation 21 | Formulation 22 | Formulation 23 | Formulation 24 | Formulation 25 |
|---|---|---|---|---|---|---|
| A | Nonanal | 34.0-36.0 | 45.0-48.0 | 46.0-50.0 | 40.0-42.0 | 40.0-52.0 |
|  | Decanal | 14.0-16.0 | 18.0-21.0 | 20.0-23.0 | 16.0-18.0 | 12.0-18.0 |
|  | Heptanal | 27.0-30.0 | 8.0-9.0 | 2.0-4.0 | 4.0-6.0 | 3.0-8.0 |
|  | Octanal | 2.0-4.0 | — | 5.0-7.0 | — | 8.0-13.0 |
|  | Benzaldehyde | 2.0-4.0 | — | 2.0-3.0 | 1.0-3.0 | 3.0-7.0 |
|  | Undecanal | — | — | — | 10.0-12.0 | — |
| B | 6-Methyl-5-hepten-2-one | 7.0-9.0 | 9.0-11.0 | 6.0-9.0 | 4.0-6.0 | 6.0-11.0 |
|  | 1-Phenylethanone | — | 1.0-3.0 | 2.0-4.0 | — | — |
|  | 2-Decanone | — | — | — | 1.0-2.0 | — |
| C | Limonene | 2.0-4.0 | 1.0-3.0 | 2.0-3.0 | — | 2.0-6.0 |
|  | 1,8-Cineole | 3.0-5.0 | 1.0-2.0 | — | — | 2.0-10.0 |
|  | Menthol | 2.0-4.0 | 5.0-7.0 | 5.0-7.0 | 16.0-18.0 | 2.0-5.0 |
|  | Nonanoic acid | — | 3.0-5.0 | — | — | — |
|  | p-Cymene | — | — | — | 1.0-2.0 | — |
|  | Total | (The total mass is adjusted to be 100.0% by mass.) | | | | |

(Unit: % by mass)

Formulation with Ten Compounds

TABLE 7

| Ingredient | Chemical Compound | Formulation 26 | Formulation 27 | Formulation 28 | Formulation 29 |
|---|---|---|---|---|---|
| A | Nonanal | 34.77 | 46.12 | 47.83 | 40.88 |
|  | Decanal | 14.32 | 19.23 | 21.75 | 17.68 |
|  | Heptanal | 27.47 | 9.01 | 2.85 | 4.99 |
|  | Octanal | 2.30 | 0.00 | 5.77 | 0.00 |
|  | Benzaldehyde | 2.38 | 0.00 | 2.04 | 1.55 |
|  | Undecanal | 0.00 | 0.68 | 2.00 | 10.42 |
| B | 6-Methyl-5-hepten-2-one | 7.56 | 9.50 | 7.76 | 4.48 |
|  | 1-Phenylethanone | 1.87 | 1.77 | 2.34 | 0.00 |
|  | 2-Decanone | 0.00 | 0.00 | 0.00 | 1.12 |
| C | Limonene | 2.58 | 1.90 | 2.11 | 0.00 |
|  | 1,8-Cineole | 3.62 | 1.37 | 0.00 | 0.00 |
|  | Menthol | 3.13 | 6.55 | 5.55 | 17.16 |
|  | Nonanoic acid | 0.00 | 3.87 | 0.00 | 0.70 |
|  | p-Cymene | 0.00 | 0.00 | 0.00 | 1.02 |
|  | Total | 100.0 | 100.0 | 100.0 | 100.0 |

(Unit: % by mass)

TABLE 8

| Ingredient | Chemical Compound | Formulation 30 | Formulation 31 | Formulation 32 | Formulation 33 | Formulation 34 |
|---|---|---|---|---|---|---|
| A | Nonanal | 33.0-35.0 | 45.0-47.0 | 46.0-49.0 | 40.0-42.0 | 40.0-52.0 |
|  | Decanal | 13.0-15.0 | 18.0-20.0 | 20.0-22.0 | 17.0-20.0 | 12.0-18.0 |
|  | Heptanal | 25.0-28.0 | 8.0-10.0 | 2.0-5.0 | 4.0-6.0 | 3.0-8.0 |
|  | Octanal | 2.0-3.0 | — | 5.0-7.0 | — | 8.0-13.0 |

TABLE 8-continued

| Ingredient | Chemical Compound | Formulation 30 | Formulation 31 | Formulation 32 | Formulation 33 | Formulation 34 |
|---|---|---|---|---|---|---|
|  | Benzaldehyde | 2.0-4.0 | — | 2.0-4.0 | 1.0-3.0 | 3.0-7.0 |
|  | Undecanal | — | 0.5-1.5 | 1.0-3.0 | 10.0-12.0 | — |
| B | 6-Methyl-5-hepten-2-one | 7.0-9.0 | 9.0-11.0 | 7.0-9.0 | 4.0-6.0 | 6.0-11.0 |
|  | 1-Phenylethanone | 1.0-3.0 | 1.0-3.0 | 2.0-4.0 | — | 0.5-2.0 |
|  | 2-Decanone | — | — | — | 1.0-2.0 | — |
| C | Limonene | 2.0-4.0 | 1.0-3.0 | 2.0-3.0 | — | 2.0-6.0 |
|  | 1,8-Cineole | 3.0-5.0 | 1.0-2.0 | — | — | 2.0-10.0 |
|  | Menthol | 3.0-4.0 | 5.0-7.0 | 5.0-7.0 | 17.0-19.0 | 2.0-5.0 |
|  | Nonanoic acid | — | 3.0-5.0 | — | 0.5-1.5 | — |
|  | p-Cymene | — | — | — | 1.0-2.0 | — |
|  | Total | (The total mass is adjusted to be 100.0% by mass.) | | | | |

(Unit: % by mass)

Formulation with 13 Compounds

TABLE 9

| Ingredient | Chemical Compound | Formulation 35 | Formulation 36 | Formulation 37 | Formulation 38 | Formulation 43 |
|---|---|---|---|---|---|---|
| A | Nonanal | 40.10 | 37.16 | 31.78 | 34.04 | 34.40 |
|  | Decanal | 3.48 | 3.97 | 8.02 | 2.53 | 4.80 |
|  | Heptanal | 10.10 | 2.58 | 3.38 | 5.40 | 3.80 |
|  | Octanal | 3.77 | 3.73 | 1.91 | 3.24 | 2.90 |
|  | Benzaldehyde | 5.73 | 4.82 | 3.44 | 1.34 | 3.20 |
| B | 6-Methyl-5-hepten-2-one | 7.83 | 3.12 | 5.19 | 3.50 | 3.90 |
|  | Cyclohexanone | 2.55 | 0.00 | 0.00 | 0.00 | 0.00 |
| C | Menthol | 3.70 | 1.93 | 2.21 | 2.15 | 2.10 |
|  | Dodecane | 10.06 | 9.01 | 12.50 | 17.55 | 13.00 |
|  | Hexanoic acid | 0.00 | 9.25 | 11.99 | 6.65 | 9.30 |
|  | Octanoic acid | 6.81 | 7.65 | 8.12 | 11.45 | 9.10 |
|  | Nonanoic acid | 1.35 | 7.08 | 9.26 | 8.20 | 8.20 |
|  | 2(5H)-Furanone | 1.76 | 0.00 | 0.00 | 0.00 | 0.00 |
|  | 1-Octanol | 2.76 | 4.72 | 1.36 | 1.40 | 2.50 |
|  | 3-Hexyn-1-ol | 0.00 | 4.98 | 0.84 | 2.55 | 2.80 |
|  | Total | 100.0 | 100.0 | 100.0 | 100.0 | 100.0 |

(Unit: % by mass)

TABLE 10

| Ingredient | Chemical Compound | Formulation 39 | Formulation 40 |
|---|---|---|---|
| A | Nonanal | 35.0-45.0 | 30.0-40.0 |
|  | Decanal | 2.0-6.0 | 2.0-10.0 |
|  | Heptanal | 7.0-15.0 | 2.0-7.0 |
|  | Octanal | 2.0-6.0 | 1.0-5.0 |
|  | Benzaldehyde | 5.0-10.0 | 1.0-6.0 |
| B | 6-Methyl-5-hepten-2-one | 3.0-10.0 | 2.0-7.0 |
|  | Cyclohexanone | 1.0-6.0 | — |
| C | Menthol | 2.0-5.0 | 1.0-3.0 |
|  | Dodecane | 7.0-15.0 | 8.0-18.0 |
|  | Hexanoic acid | — | 6.0-13.0 |
|  | Octanoic acid | 3.0-8.0 | 7.0-12.0 |

TABLE 10-continued

| Ingredient | Chemical Compound | Formulation 39 | Formulation 40 |
|---|---|---|---|
|  | Nonanoic acid | 1.0-3.0 | 5.0-10.0 |
|  | 2(5H)-Furanone | 1.0-4.0 | — |
|  | 1-Octanol | 1.0-3.0 | 1.0-6.0 |
|  | 3-Hexyn-1-ol | — | 0.5-7.0 |
|  | Total | (The total mass is adjusted to be 100.0% by mass.) | |

(Unit: % by mass)

Formulation with 14 Compounds

TABLE 11

| Ingredient | Chemical Compound | Formulation 41 | Formulation 42 | Formulation 44 | Formulation 45 |
|---|---|---|---|---|---|
| A | Nonanal | 22.59 | 20.0-25.0 | 31.50 | 27.0-42.0 |
|  | Decanal | 6.20 | 4.0-8.0 | 4.80 | 4.0-8.0 |
|  | Heptanal | 4.03 | 2.0-7.0 | 7.10 | 5.0-10.0 |
|  | Octanal | 2.85 | 2.0-5.0 | 3.30 | 2.0-5.0 |
|  | Benzaldehyde | 5.88 | 2.0-6.0 | 5.80 | 2.0-6.0 |
| B | 6-Methyl-5-hepten-2-one | 7.28 | 3.0-10.0 | 7.60 | 3.0-10.0 |
|  | Cyclohexanone | 4.90 | 2.0-8.0 | 3.70 | 2.0-8.0 |
| C | Limonene | 15.32 | 10.0-20.0 | 7.50 | 5.0-15.0 |
|  | Menthol | 2.99 | 2.0-5.0 | 3.40 | 2.0-5.0 |
|  | Dodecane | 15.00 | 10.0-18.0 | 12.40 | 10.0-18.0 |
|  | Octanoic acid | 3.95 | 2.0-5.0 | 5.40 | 3.0-7.0 |

TABLE 11-continued

| Ingredient | Chemical Compound | Formulation 41 | Formulation 42 | Formulation 44 | Formulation 45 |
|---|---|---|---|---|---|
| | Nonanoic acid | 3.15 | 1.0-5.0 | 2.30 | 1.0-5.0 |
| | 2(5H)-Furanone | 3.70 | 2.0-5.0 | 2.70 | 2.0-5.0 |
| | 1-Octanol | 2.16 | 1.0-3.0 | 2.50 | 1.0-3.0 |
| | Total | 100.0 | * | 100.0 | * |

(Unit: % by mass)
*The total mass is adjusted to be 100.0% by mass.

Second Embodiment

Formulation with 15 Compounds

TABLE 12-1

| Ingredient | Chemical Compound | #1501 | #1502 | #1503 | #1504 | #1505 | #1506 | #1509 | #1510 | #1511 | #1512 |
|---|---|---|---|---|---|---|---|---|---|---|---|
| A2 | Hexanal | 2.9 | 0.9 | 2.3 | 3.6 | 0.9 | 1.7 | 1.8 | 1.0 | 6.9 | 1.3 |
| A2 | Heptanal | 1.3 | 1.6 | 1.6 | 2.0 | 1.8 | 1.4 | 3.2 | 1.2 | 3.2 | 1.4 |
| A2 | Benzaldehyde | 0.7 | 2.2 | 0.8 | 1.3 | 0.6 | 0.2 | 1.3 | 0.3 | 0.7 | 1.0 |
| B | 6-Methyl-5-hepten-2-one | 16.0 | 8.1 | 3.6 | 6.2 | 7.4 | 5.1 | 5.9 | 3.8 | 2.7 | 10.3 |
| A2 | Octanal | 5.8 | 1.2 | 3.9 | 4.7 | 4.8 | 4.4 | 6.8 | 5.3 | 6.6 | 8.4 |
| C | Hexanoic acid | 0.0 | 0.0 | 0.3 | 0.0 | 0.0 | 0.0 | 0.0 | 0.0 | 0.0 | 0.0 |
| C | p-Cymene | 0.8 | 2.0 | 0.8 | 0.7 | 0.0 | 0.4 | 1.7 | 0.6 | 0.5 | 0.2 |
| C | 1,8-Cineole | 0.0 | 3.9 | 0.0 | 0.0 | 1.1 | 0.0 | 0.0 | 0.0 | 0.0 | 0.0 |
| C | Limonene | 1.2 | 2.8 | 0.4 | 1.7 | 1.5 | 18.5 | 1.0 | 4.3 | 0.6 | 1.2 |
| B | 1-Phenylethanone | 1.0 | 1.9 | 0.0 | 1.7 | 1.1 | 0.2 | 1.2 | 0.0 | 0.6 | 0.0 |
| A1 | Nonanal | 49.2 | 48.8 | 47.0 | 50.9 | 58.7 | 35.4 | 45.5 | 52.1 | 49.5 | 27.6 |
| C | 2-Nonen-1-ol | 2.5 | 1.9 | 0.0 | 3.2 | 0.6 | 4.0 | 2.6 | 2.4 | 1.7 | 11.5 |
| C | Menthol | 2.0 | 3.3 | 13.9 | 4.5 | 5.1 | 0.0 | 3.6 | 3.8 | 2.8 | 2.7 |
| B | 2-Decanone | 0.0 | 0.9 | 1.3 | 0.5 | 0.7 | 2.1 | 2.0 | 1.4 | 1.1 | 0.9 |
| A2 | Decanal | 10.5 | 15.1 | 14.0 | 17.2 | 14.6 | 10.0 | 15.0 | 15.4 | 15.4 | 14.8 |
| C | Octanoic acid | 0.0 | 0.0 | 0.0 | 0.0 | 0.0 | 0.0 | 0.0 | 0.0 | 0.0 | 0.0 |
| B | 2-Undecanone | 2.3 | 0.0 | 0.4 | 0.0 | 0.0 | 0.7 | 1.5 | 2.1 | 0.6 | 0.7 |
| C | Nonanoic acid | 1.8 | 0.0 | 1.1 | 0.3 | 0.7 | 1.9 | 0.0 | 0.0 | 0.0 | 0.3 |
| A2 | Undecanal | 2.1 | 5.5 | 8.4 | 1.6 | 0.5 | 13.9 | 6.8 | 5.5 | 7.1 | 17.6 |
| | Total | 100.0 | 100.0 | 100.0 | 100.0 | 100.0 | 100.0 | 100.0 | 100.0 | 100.0 | 100.0 |

TABLE 12-2

| Ingredient | Chemical Compound | #1513 | #1517 | #1521 | #1525 | #1527 | #1528 | #1529 | #1530 | #1532 |
|---|---|---|---|---|---|---|---|---|---|---|
| A2 | Hexanal | 2.8 | 0.4 | 1.0 | 0.6 | 0.0 | 0.3 | 1.4 | 0.6 | 0.4 |
| A2 | Heptanal | 0.5 | 0.6 | 3.1 | 2.8 | 0.6 | 0.8 | 1.3 | 0.9 | 2.4 |
| A2 | Benzaldehyde | 0.3 | 0.0 | 1.3 | 0.9 | 1.0 | 0.2 | 0.7 | 0.0 | 0.3 |
| B | 6-Methyl-5-hepten-2-one | 1.3 | 2.8 | 3.4 | 4.9 | 8.2 | 3.1 | 7.8 | 2.3 | 6.3 |
| A2 | Octanal | 3.1 | 3.0 | 4.8 | 4.2 | 3.3 | 3.1 | 5.3 | 3.6 | 3.7 |
| C | Hexanoic acid | 0.0 | 0.0 | 0.0 | 0.0 | 0.0 | 0.0 | 0.0 | 0.0 | 0.0 |
| C | p-Cymene | 0.2 | 3.2 | 0.2 | 0.5 | 0.3 | 0.2 | 0.2 | 0.3 | 0.2 |
| C | 1,8-Cineole | 0.0 | 25.0 | 0.0 | 0.6 | 0.0 | 0.0 | 0.0 | 0.3 | 0.0 |
| C | Limonene | 3.5 | 5.4 | 6.6 | 7.9 | 3.7 | 4.0 | 2.8 | 2.7 | 2.1 |
| B | 1-Phenylethanone | 0.0 | 1.7 | 0.3 | 0.5 | 0.0 | 0.0 | 1.1 | 0.9 | 0.1 |
| A1 | Nonanal | 56.0 | 40.9 | 48.5 | 47.8 | 43.5 | 56.9 | 55.8 | 58.9 | 59.2 |
| C | 2-Nonen-1-ol | 7.0 | 1.7 | 2.6 | 2.3 | 6.0 | 9.7 | 2.7 | 8.4 | 3.1 |
| C | Menthol | 2.4 | 2.1 | 0.0 | 2.9 | 2.9 | 2.9 | 1.9 | 2.6 | 0.0 |
| B | 2-Decanone | 0.9 | 1.1 | 0.8 | 0.6 | 0.8 | 0.4 | 1.5 | 0.5 | 1.8 |
| A2 | Decanal | 15.3 | 6.9 | 15.0 | 8.5 | 21.7 | 10.5 | 13.1 | 10.7 | 13.3 |
| C | Octanoic acid | 0.0 | 0.0 | 0.0 | 0.0 | 0.0 | 0.0 | 0.0 | 0.0 | 0.0 |
| B | 2-Undecanone | 1.0 | 0.0 | 0.4 | 0.3 | 0.1 | 0.0 | 0.1 | 0.3 | 0.0 |
| C | Nonanoic acid | 0.1 | 1.9 | 2.1 | 0.0 | 0.3 | 0.1 | 0.0 | 0.0 | 0.2 |
| A2 | Undecanal | 5.7 | 3.5 | 9.9 | 15.2 | 7.3 | 7.7 | 4.1 | 7.0 | 6.9 |
| | Total | 100.0 | 100.0 | 100.0 | 100.0 | 100.0 | 100.0 | 100.0 | 100.0 | 100.0 |

Formulation with Nine Compounds

TABLE 13-1

| Ingredient | Chemical Compound | #901 | #902 | #903 | #904 | #905 | #906 | #909 | #910 | #911 | #912 |
|---|---|---|---|---|---|---|---|---|---|---|---|
| A2 | Hexanal | 3.1 | 0.0 | 2.4 | 3.9 | 0.0 | 0.0 | 0.0 | 0.0 | 7.2 | 1.4 |
| A2 | Heptanal | 0.0 | 0.0 | 1.7 | 2.1 | 1.8 | 0.0 | 3.5 | 0.0 | 3.3 | 1.5 |
| A2 | Benzaldehyde | 0.0 | 2.4 | 0.0 | 0.0 | 0.0 | 0.0 | 0.0 | 0.0 | 0.0 | 0.0 |
| B | 6-Methyl-5-hepten-2-one | 17.1 | 8.8 | 3.8 | 6.6 | 7.7 | 5.3 | 6.5 | 4.1 | 2.8 | 10.8 |
| A2 | Octanal | 6.2 | 0.0 | 4.1 | 5.0 | 5.0 | 4.7 | 7.4 | 5.5 | 6.9 | 8.7 |
| C | Hexanoic acid | 0.0 | 0.0 | 0.0 | 0.0 | 0.0 | 0.0 | 0.0 | 0.0 | 0.0 | 0.0 |
| C | p-Cymene | 0.0 | 2.2 | 0.0 | 0.0 | 0.0 | 0.0 | 0.0 | 0.0 | 0.0 | 0.0 |
| C | 1,8-Cineole | 0.0 | 4.2 | 0.0 | 0.0 | 0.0 | 1.1 | 0.0 | 0.0 | 0.0 | 0.0 |
| C | Limonene | 0.0 | 3.0 | 0.0 | 0.0 | 1.5 | 19.4 | 0.0 | 4.5 | 0.0 | 0.0 |
| B | 1-Phenylethanone | 0.0 | 0.0 | 0.0 | 1.8 | 1.2 | 0.0 | 0.0 | 0.0 | 0.0 | 0.0 |
| A1 | Nonanal | 52.8 | 53.3 | 48.9 | 54.2 | 61.1 | 37.1 | 49.8 | 55.0 | 51.6 | 28.9 |
| C | 2-Nonen-1-ol | 2.7 | 0.0 | 0.0 | 3.4 | 0.0 | 4.2 | 2.9 | 2.6 | 1.8 | 12.0 |
| C | Menthol | 2.1 | 3.7 | 14.4 | 4.8 | 5.3 | 0.0 | 4.0 | 4.0 | 2.9 | 2.8 |
| B | 2-Decanone | 0.0 | 0.0 | 1.4 | 0.0 | 0.0 | 2.2 | 2.1 | 0.0 | 0.0 | 0.0 |
| A2 | Decanal | 11.3 | 16.5 | 14.6 | 18.3 | 15.2 | 10.5 | 16.4 | 16.2 | 16.1 | 15.4 |
| C | Octanoic acid | 0.0 | 0.0 | 0.0 | 0.0 | 0.0 | 0.0 | 0.0 | 0.0 | 0.0 | 0.0 |
| B | 2-Undecanone | 2.5 | 0.0 | 0.0 | 0.0 | 0.0 | 0.0 | 0.0 | 2.2 | 0.0 | 0.0 |
| C | Nonanoic acid | 0.0 | 0.0 | 0.0 | 0.0 | 0.0 | 2.0 | 0.0 | 0.0 | 0.0 | 0.0 |
| A2 | Undecanal | 2.3 | 6.0 | 8.8 | 0.0 | 0.0 | 14.6 | 7.4 | 5.8 | 7.4 | 18.4 |
|  | Total | 100.0 | 100.0 | 100.0 | 100.0 | 100.0 | 100.0 | 100.0 | 100.0 | 100.0 | 100.0 |

TABLE 13-2

| Ingredient | Chemical Compound | #913 | #917 | #921 | #925 | #927 | #928 | #929 | #930 | #932 |
|---|---|---|---|---|---|---|---|---|---|---|
| A2 | Hexanal | 2.9 | 0.0 | 0.0 | 0.0 | 0.0 | 0.0 | 0.0 | 0.0 | 0.0 |
| A2 | Heptanal | 0.0 | 0.0 | 3.3 | 2.9 | 0.0 | 0.8 | 0.0 | 0.0 | 2.5 |
| A2 | Benzaldehyde | 0.0 | 0.0 | 0.0 | 0.0 | 1.0 | 0.0 | 0.0 | 0.0 | 0.0 |
| B | 6-Methyl-5-hepten-2-one | 1.3 | 3.0 | 3.5 | 5.1 | 8.4 | 3.1 | 8.2 | 2.3 | 6.3 |
| A2 | Octanal | 3.2 | 3.2 | 5.0 | 4.3 | 3.3 | 3.2 | 5.6 | 3.7 | 3.7 |
| C | Hexanoic acid | 0.0 | 0.0 | 0.0 | 0.0 | 0.0 | 0.0 | 0.0 | 0.0 | 0.0 |
| C | p-Cymene | 0.0 | 3.4 | 0.0 | 0.0 | 0.0 | 0.0 | 0.0 | 0.0 | 0.0 |
| C | 1,8-Cineole | 0.0 | 26.9 | 0.0 | 0.0 | 0.0 | 0.0 | 0.0 | 0.0 | 0.0 |
| C | Limonene | 3.6 | 5.9 | 6.9 | 8.2 | 3.8 | 4.1 | 3.0 | 2.8 | 2.1 |
| B | 1-Phenylethanone | 0.0 | 0.0 | 0.0 | 0.0 | 0.0 | 0.0 | 0.0 | 1.1 | 0.0 |
| A1 | Nonanal | 57.7 | 44.1 | 50.5 | 49.6 | 44.6 | 57.7 | 58.7 | 60.6 | 59.9 |
| C | 2-Nonen-1-ol | 7.2 | 0.0 | 2.7 | 2.4 | 6.2 | 9.9 | 2.8 | 8.6 | 3.1 |
| C | Menthol | 2.5 | 2.2 | 0.0 | 3.0 | 2.9 | 2.9 | 2.1 | 2.6 | 0.0 |
| B | 2-Decanone | 0.0 | 0.0 | 0.0 | 0.0 | 0.0 | 0.0 | 1.6 | 0.0 | 1.8 |
| A2 | Decanal | 15.7 | 7.4 | 15.7 | 8.8 | 22.2 | 10.6 | 13.8 | 11.0 | 13.4 |
| C | Octanoic acid | 0.0 | 0.0 | 0.0 | 0.0 | 0.0 | 0.0 | 0.0 | 0.0 | 0.0 |
| B | 2-Undecanone | 0.0 | 0.0 | 0.0 | 0.0 | 0.0 | 0.0 | 0.0 | 0.0 | 0.0 |
| C | Nonanoic acid | 0.0 | 0.0 | 2.2 | 0.0 | 0.0 | 0.0 | 0.0 | 0.0 | 0.0 |
| A2 | Undecanal | 5.9 | 3.8 | 10.3 | 15.8 | 7.4 | 7.8 | 4.3 | 7.2 | 7.0 |
|  | Total | 100.0 | 100.0 | 100.0 | 100.0 | 100.0 | 100.0 | 100.0 | 100.0 | 100.0 |

Formulation with Eight Compounds

TABLE 14-1

| Ingredient | Chemical Compound | #801 | #802 | #803 | #804 | #805 | #806 | #809 | #810 | #811 | #812 |
|---|---|---|---|---|---|---|---|---|---|---|---|
| A2 | Hexanal | 3.2 | 0.0 | 2.5 | 3.9 | 0.0 | 0.0 | 0.0 | 0.0 | 7.3 | 0.0 |
| A2 | Heptanal | 0.0 | 0.0 | 1.7 | 2.1 | 1.9 | 0.0 | 3.6 | 0.0 | 3.4 | 1.5 |
| A2 | Benzaldehyde | 0.0 | 2.5 | 0.0 | 0.0 | 0.0 | 0.0 | 0.0 | 0.0 | 0.0 | 0.0 |
| B | 6-Methyl-5-hepten-2-one | 17.5 | 9.0 | 3.8 | 6.7 | 7.8 | 5.4 | 6.6 | 4.2 | 2.8 | 11.0 |
| A2 | Octanal | 6.3 | 0.0 | 4.1 | 5.0 | 5.1 | 4.8 | 7.6 | 5.7 | 7.0 | 8.9 |
| C | Hexanoic acid | 0.0 | 0.0 | 0.0 | 0.0 | 0.0 | 0.0 | 0.0 | 0.0 | 0.0 | 0.0 |
| C | p-Cymene | 0.0 | 0.0 | 0.0 | 0.0 | 0.0 | 0.0 | 0.0 | 0.0 | 0.0 | 0.0 |
| C | 1,8-Cineole | 0.0 | 4.3 | 0.0 | 0.0 | 0.0 | 0.0 | 0.0 | 0.0 | 0.0 | 0.0 |
| C | Limonene | 0.0 | 3.1 | 0.0 | 0.0 | 1.6 | 19.8 | 0.0 | 4.6 | 0.0 | 0.0 |
| B | 1-Phenylethanone | 0.0 | 0.0 | 0.0 | 0.0 | 1.2 | 0.0 | 0.0 | 0.0 | 0.0 | 0.0 |
| A1 | Nonanal | 53.9 | 54.5 | 49.6 | 55.2 | 61.8 | 37.9 | 50.9 | 56.3 | 52.6 | 29.3 |
| C | 2-Nonen-1-ol | 2.7 | 0.0 | 0.0 | 3.5 | 0.0 | 4.2 | 3.0 | 2.6 | 0.0 | 12.2 |
| C | Menthol | 0.0 | 3.7 | 14.6 | 4.8 | 5.4 | 0.0 | 4.0 | 4.1 | 2.9 | 2.8 |

TABLE 14-1-continued

| Ingredient | Chemical Compound | #801 | #802 | #803 | #804 | #805 | #806 | #809 | #810 | #811 | #812 |
|---|---|---|---|---|---|---|---|---|---|---|---|
| B | 2-Decanone | 0.0 | 0.0 | 0.0 | 0.0 | 0.0 | 2.3 | 0.0 | 0.0 | 0.0 | 0.0 |
| A2 | Decanal | 11.5 | 16.8 | 14.8 | 18.6 | 15.3 | 10.7 | 16.7 | 16.6 | 16.4 | 15.6 |
| C | Octanoic acid | 0.0 | 0.0 | 0.0 | 0.0 | 0.0 | 0.0 | 0.0 | 0.0 | 0.0 | 0.0 |
| B | 2-Undecanone | 2.5 | 0.0 | 0.0 | 0.0 | 0.0 | 0.0 | 0.0 | 0.0 | 0.0 | 0.0 |
| C | Nonanoic acid | 0.0 | 0.0 | 0.0 | 0.0 | 0.0 | 0.0 | 0.0 | 0.0 | 0.0 | 0.0 |
| A2 | Undecanal | 2.3 | 6.1 | 8.9 | 0.0 | 0.0 | 14.9 | 7.6 | 5.9 | 7.6 | 18.7 |
| | Total | 100.0 | 100.0 | 100.0 | 100.0 | 100.0 | 100.0 | 100.0 | 100.0 | 100.0 | 100.0 |

TABLE 14-2

| Ingredient | Chemical Compound | #817 | #821 | #825 | #827 | #828 | #829 | #830 | #832 |
|---|---|---|---|---|---|---|---|---|---|
| A2 | Hexanal | 0.0 | 0.0 | 0.0 | 0.0 | 0.0 | 0.0 | 0.0 | 0.0 |
| A2 | Heptanal | 0.0 | 3.3 | 2.9 | 0.0 | 0.0 | 0.0 | 0.0 | 2.5 |
| A2 | Benzaldehyde | 0.0 | 0.0 | 0.0 | 0.0 | 0.0 | 0.0 | 0.0 | 0.0 |
| B | 6-Methyl-5-hepten-2-one | 3.1 | 3.6 | 5.2 | 8.5 | 3.2 | 8.3 | 2.3 | 6.5 |
| A2 | Octanal | 3.3 | 5.1 | 4.4 | 3.4 | 3.2 | 5.7 | 3.7 | 3.8 |
| C | Hexanoic acid | 0.0 | 0.0 | 0.0 | 0.0 | 0.0 | 0.0 | 0.0 | 0.0 |
| C | p-Cymene | 3.5 | 0.0 | 0.0 | 0.0 | 0.0 | 0.0 | 0.0 | 0.0 |
| C | 1,8-Cineole | 27.5 | 0.0 | 0.0 | 0.0 | 0.0 | 0.0 | 0.0 | 0.0 |
| C | Limonene | 6.0 | 7.1 | 8.4 | 3.8 | 4.1 | 3.0 | 2.8 | 2.2 |
| B | 1-Phenylethanone | 0.0 | 0.0 | 0.0 | 0.0 | 0.0 | 0.0 | 0.0 | 0.0 |
| A1 | Nonanal | 45.1 | 51.6 | 50.8 | 45.1 | 58.1 | 59.7 | 61.3 | 61.1 |
| C | 2-Nonen-1-ol | 0.0 | 2.7 | 0.0 | 6.3 | 10.0 | 2.9 | 8.7 | 3.2 |
| C | Menthol | 0.0 | 0.0 | 3.1 | 3.0 | 2.9 | 2.1 | 2.7 | 0.0 |
| B | 2-Decanone | 0.0 | 0.0 | 0.0 | 0.0 | 0.0 | 0.0 | 0.0 | 0.0 |
| A2 | Decanal | 7.6 | 16.0 | 9.0 | 22.5 | 10.7 | 14.0 | 11.1 | 13.7 |
| C | Octanoic acid | 0.0 | 0.0 | 0.0 | 0.0 | 0.0 | 0.0 | 0.0 | 0.0 |
| B | 2-Undecanone | 0.0 | 0.0 | 0.0 | 0.0 | 0.0 | 0.0 | 0.0 | 0.0 |
| C | Nonanoic acid | 0.0 | 0.0 | 0.0 | 0.0 | 0.0 | 0.0 | 0.0 | 0.0 |
| A2 | Undecanal | 3.9 | 10.5 | 16.2 | 7.5 | 7.8 | 4.4 | 7.3 | 7.1 |
| | Total | 100.0 | 100.0 | 100.0 | 100.0 | 100.0 | 100.0 | 100.0 | 100.0 |

In Tables 12-1, 12-2, 13-1, 13-2, 14-1, and 14-2, a 4-digit or 3-digit number following the number symbol "#" means a formulation number. For each formulation number, each of the leading numbers "15", "9", and "8" means the number of chemical compounds, and the last 2-digit number ("01", "02", or the like) means the line of formulation. That is, preferred forms according to the second embodiment of the present invention described in Tables 12-1, 12-2, 13-1, 13-2, 14-1, and 14-2 are classified into 19 lines represented by the numbers "01" to "32", and for each of the lines, there are formulation with 15 compounds, formulation with nine compounds, and formulations with eight compounds. Note that for the line "13", there is no formulation with eight compounds, but there are formulation with 15 compounds and formulation with nine compounds. Formulations belonging to the same line are different in the number of chemical compounds used, but are similar to each other in the tendency of a scent. That is, for example, an effect of an odorant composition formulated with 15 compounds belonging to a certain line is also exhibited similarly by formulation with nine compounds or eight compounds belonging to the same line. In addition, there is a similarity in the tendency of a scent among lines. Specifically, although there are differences in the kinds and blending ratios of individual chemical compounds among 14 lines in total including "02", "04", "05", "09", "10", "11", "13", "21", "25", "27", "28", "29", "30", and "32", effects exhibited as a whole odorant composition are similar. In other words, formulations belonging to these lines are within a standard formulation of the odorant composition according to the second embodiment of the present invention. The above-described matters will be explained more specifically in Examples described later.

The odorant composition of the present invention can be blended with perfumery and cosmetics, food and drink, a tobacco product, an ink, a drawing material, or the like as it is, in a state of being diluted with various solvents, or in a state of being combined with a liquid base material, a mist base material, a gel base material, a solid base material, paper, a fiber, a capsule, or the like.

Examples of a solvent for dilution include: water; an alcohol such as ethanol or glycerin, a glycol such as ethylene glycol, propylene glycol, or dipropylene glycol; and vegetable fats and oils.

When a solvent is used, a dilution ratio of the odorant composition is not particularly limited, and can be appropriately adjusted based on the kind of a chemical compound contained in the odorant composition, a blending ratio of the chemical compound, and the like. Examples of the dilution ratio include 1%, 0.1%, 0.01%, a range of 0.5% to 1%, a range of 0.1% to 0.5%, a range of 0.05% to 0.1%, a range of 0.01% to 0.05%, and a range of 0.005% to 0.01%.

Examples of the liquid base material and the mist base material include: water; an alcohol such as ethanol; a glycol such as ethylene glycol, propylene glycol, or dipropylene glycol; an aliphatic ester such as isopropyl myristate or triethyl citrate; an aromatic ester such as diethyl phthalate, dibutyl phthalate, or benzyl benzoate; a nonionic surfactant such as polyoxyethylene sorbitan monostearate; an anionic surfactant such as sodium polyoxylauryl ether phosphate;

and a cationic surfactant such as lauryltrimethylammonium chloride or distearyldimethylammonium chloride.

Examples of the gel base material include: gelling agents extracted from various plants, animals, algae, microorganisms, and the like, such as carrageenan, gellan gum, tragacanth gum, agar, gelatin, and pectin; a metal soap used as a gelling agent, such as sodium stearate; and those formed from a water-soluble organic polymer such as polyvinyl alcohol or a cellulose derivative.

Examples of the solid base material include a powder or a granular molded product of a material having physical adsorption capability and a large specific surface area, such as silica gel, alumina, or activated carbon.

Examples of the capsule include: a capsule having an outer diameter of about 1 mm to several hundred mm; a microcapsule having an outer diameter of about 1 μm to 1000 μm; and a nanocapsule having an outer diameter of about 1 nm to 1000 nm. The kind, thickness, hardness, and the like of a wall material (material of a capsule wall) for containing the odorant composition are not particularly limited, and can be appropriately selected and adjusted according to use of a capsule (a microcapsule or a nanocapsule). The outer diameter of a capsule (a microcapsule or a nanocapsule) containing the odorant composition of the present invention can be measured using an electron microscope or the like after being dried and formed into a powder.

The perfumery and cosmetics according to the present invention is not particularly limited, and examples thereof include: a perfume; a hair care product such as a shampoo, a rinse, or a hairdressing (a hair cream, a pomade, or the like); cosmetics such as a foundation, a lipstick, a lip cream, a lip gloss, a lotion, a cosmetic emulsion, a cosmetic cream, a cosmetic gel, a serum, a pack, an antiperspirant, and a deodorant; a health and hygiene detergent such as a face soap, a body soap, a bath agent, a laundry soap, a laundry detergent, a disinfectant detergent, or a deodorant detergent; a health and hygiene material such as an oral composition (a dentifrice, an oral cleanser, a mouthwash, a troche, a chewing gum, or the like), tissue paper, toilet paper, a diaper (a paper diaper, a diaper cover, or the like), a sanitary product (a napkin, a tampon, or the like), a first-aid product (gauze, a first-aid adhesive plaster, a cotton swab, or the like), a cleaning product (wet tissue, cosmetic cotton, breast milk pad, or the like), a wet towel, or a mask; and an aromatic product such as an interior aromatic agent or a car colon.

The form (dosage form) of the perfumery and cosmetics is not particularly limited, and can be applied to various forms such as a liquid form, an emulsion form, a cream form, a paste form, a solid form, and a multilayer form. In addition to these forms, the perfumery and cosmetics can also be applied as a sheet agent, a spray agent, or a mousse agent.

The food and drink according to the present invention is not particularly limited, and examples thereof include: confectionery such as caramel, candy, gum, tablet confectionery, cracker, biscuit, cookie, pie, chocolate, or snack, and mixes for producing these, such as a cake mix; a dessert such as ice cream, lact ice, sherbet, yogurt, pudding, jelly, or a daily dessert, and mixes for producing these; a dairy product such as butter, cheese, milk, or yoghurt; a soft beverage such as a fruit juice beverage, a vegetable beverage, a sports drink, a honey beverage, soy milk, a vitamin supplement beverage, a mineral supplement beverage, a nutritional drink, a nutritious drink, a lactic acid bacteria beverage, a milk beverage, or a non-alcoholic beer; a preference beverage such as green tea, black tea, oolong tea, herb tea, milk tea, or a coffee beverage; and general foods such as bread, soup, and various instant foods.

The tobacco product according to the present invention is not particularly limited, and examples thereof include a cigarette, an electronic cigarette, a heat-type cigarette, a chewing cigarette, and a snuff cigarette.

A microcapsule or a nanocapsule containing the odorant composition of the present invention can be blended in an ink, and can be used as a fragrance ink for printing. The fragrance ink of the present invention can be applied to various printing methods such as offset printing, gravure printing, letterpress printing, and stencil printing, and a printed matter using the fragrance ink can be produced.

In addition, a microcapsule or a nanocapsule containing the odorant composition of the present invention can be blended in a drawing material. Examples of the drawing material include crayon, chalk, dermatograph, black core, color core, fluorescent core, eyebrow, eyeshadow, eyeliner, and eyebrow liner.

Furthermore, the odorant composition of the present invention can be used for a material such as paper, a fabric, a woven fabric, a knitted fabric, a nonwoven fabric, a rug, a plate material, an ornament, a wrapping and packaging material (a bag for food, a decorative box, wrapping paper, packing paper, a film, a cushioning material, a string, a handle, a wrapping article (a label, a seal, or the like), or a toy (a welfare toy, an intellectual training toy, an educational toy, stationery, or the like).

EXAMPLES

Hereinafter, embodiments of the present invention will be described with reference to representative Examples, but the present invention is not limited to these Examples.
<Formulation with Eight Compounds>
[Preparation of Odorant Composition]

Chemical compounds were blended according to blending ratios (% by mass) described in Table 15 to prepare odorant compositions of Examples 1 to 4. Note that the odorant compositions of Examples 1 to 4 correspond to formulations 1 to 4 described in Table 1 above, respectively.

TABLE 15

| Ingredient | Chemical Compound | Example 1 | Example 2 | Example 3 | Example 4 |
|---|---|---|---|---|---|
| A | Nonanal | 45.40 | 50.10 | 42.41 | 51.20 |
|  | Decanal | 14.30 | 15.40 | 16.61 | 13.30 |
|  | Heptanal | 4.00 | 6.40 | 6.32 | 7.70 |
|  | Octanal | 8.60 | 11.20 | 11.92 | 9.90 |
|  | Benzaldehyde | 3.50 | 4.00 | 5.62 | 4.00 |
| B | 6-Methyl-5-hepten-2-one | 9.30 | 6.80 | 10.52 | 10.40 |
|  | 1-Phenylethanone | 0.00 | 0.00 | 0.00 | 0.90 |
| C | Limonene | 5.10 | 3.10 | 3.00 | 0.00 |
|  | 1,8-Cineole | 9.80 | 3.00 | 0.00 | 0.00 |
|  | Menthol | 0.00 | 0.00 | 3.60 | 2.60 |
|  | Total | 100.0 | 100.0 | 100.0 | 100.0 |

(Unit: % by mass)

[Sensory Evaluation 1 of Scent of Odorant Composition]

A solution was prepared by diluting each of the odorant compositions of Examples 1 to 4 to 0.01% with propylene glycol, and used as an evaluation sample. Each evaluation sample was immersed in filter paper, and for an impression of sniffing the scent, a sensory evaluation test was performed in which the degree of feeling that the scent fell under each of evaluation items described in Table 16 below was evaluated by five subjects in 11 stage of 0 point (a subject does not think at all that the sample is so) to 10 points (a subject completely thinks that the sample is so).

TABLE 16

| Symbol | Item |
| --- | --- |
| w1 | likable |
| w2 | disliked |
| w3 | pleasant |
| w4 | unpleasant |
| w5 | strong |
| w6 | pungent |
| w7 | mild |
| w8 | mellow |
| w9 | rich |
| w10 | subtle |
| w11 | sweet |
| w12 | sour/acidic |
| w13 | astringent |
| w14 | medicinal |
| w15 | fatty |
| w16 | milky |
| w17 | fermented |
| w18 | alcoholic |
| w19 | floral |
| w20 | fruity |
| w21 | refreshing |
| w22 | warm |
| w23 | cool |
| w24 | foresty |
| w25 | earthy |
| w26 | green |
| w27 | musty |
| w28 | beast-like |
| w29 | detergent-like |
| w30 | solvent-like |
| w31 | acquired |
| w32 | impressive |

Results thereof are shown in FIG. 1.

FIG. 1 is a graph showing results of sensory evaluation 1 of scents of the odorant compositions of Examples 1 to 4.

Four graphs shown in FIG. 1 are results of Example 1, Example 2, Example 3, and Example 4 in order from the left. Note that the graph shown in FIG. 1 is obtained by plotting an average value (horizontal axis) of results (scores) obtained for each evaluation item (vertical axis) for each odorant composition. The same applies to FIGS. 2 and 14 mentioned later.

As shown in FIG. 1, for all the evaluation samples of Examples 1 to 4, there was a tendency that scores were high for words indicating a positive impression (positive words) such as "likable", "pleasant", "floral", "fruity", "refreshing", and "impressive", and scores were low for words indicating a negative impression (negative words) such as "disliked", "unpleasant", "pungent", "astringent", "earthy", "musty", and "beast-like". In particular, in each of the evaluation samples of Examples 1 and 2, a result was obtained in which a difference between a score for a positive word and a score for a negative word was large. Therefore, it has been suggested that each of the evaluation samples of Examples 1 and 2 is an odorant composition having good scent palatability allowing peoples to feel comfortable.

Note that as a result of performing similar tests using evaluation samples having dilution ratios of 0.1% and 1%, a tendency similar to the above case of 0.01% was obtained. However, it has been suggested that in the odorant compositions of Examples 1 to 4, it is more preferable to set the dilution ratio to about 0.01%.

[Sensory Evaluation 2 of Scent of Odorant Composition]

In order to evaluate the degree to which a scent was appealing to an emotion of a person, evaluation items described in Table 17 below were set, an evaluation sample having a dilution ratio of 0.01% prepared in a similar manner to the sensory evaluation 1 was immersed in filter paper, and a sensory evaluation test was performed by five subjects on feeling of sniffing the scent.

TABLE 17

| Symbol | Item |
| --- | --- |
| w33 | likable |
| w34 | unpleasant |
| w35 | affectionate |
| w36 | pleasant |
| w37 | positive |
| w38 | want to protect |
| w39 | unforgettable |
| w40 | disliked |
| w41 | happy |
| w42 | addictive |
| w43 | relaxing |

Figure 2:
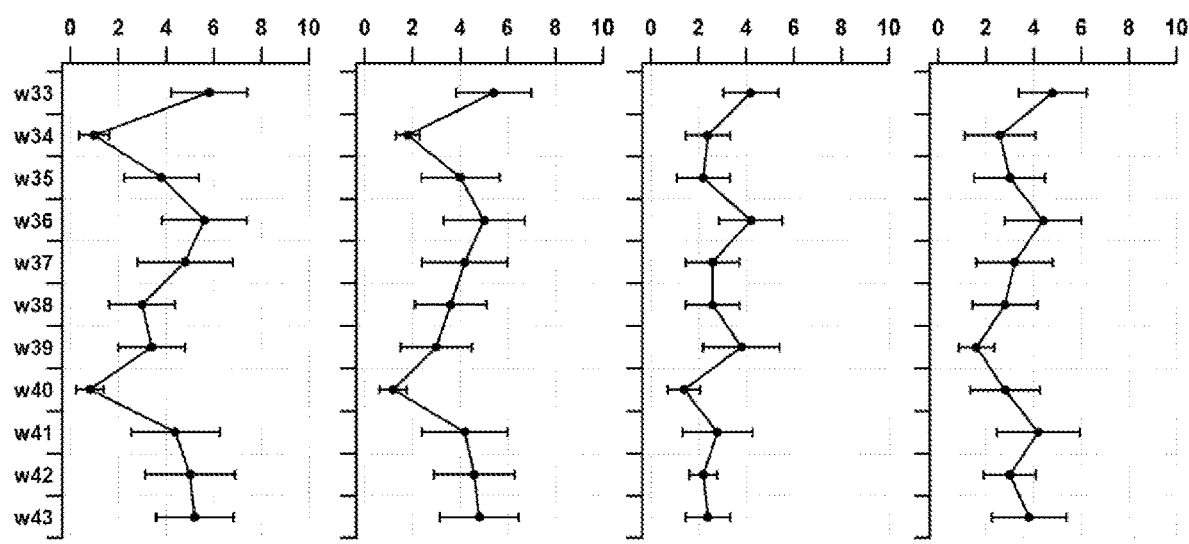
FIG. 2 is a graph showing results of sensory evaluation 2 of the scents of the odorant compositions of Examples 1 to 4.

Results thereof are shown in FIG. 2.

FIG. 2 is a graph showing results of sensory evaluation 2 of scents of the odorant compositions of Examples 1 to 4.

Four graphs shown in FIG. 2 are results of Example 1, Example 2, Example 3, and Example 4 in order from the left.

As shown in FIG. 2, for all the evaluation samples of Examples 1 to 4, there was a tendency that scores were high for words indicating a positive emotion (positive words) such as "likable", "pleasant", "positive", "addictive", and "relaxing", and scores were low for words indicating a negative emotion (negative words) such as "unpleasant" and "disliked". In particular, in each of the evaluation samples of Examples 1 and 2, a result was obtained in which a difference between a score for a positive word and a score for a negative word was large. Therefore, it has been suggested that each of the evaluation samples of Examples 1 and 2 is an odorant composition that can enhance a positive emotion of a person who has smelled the scent.

In addition, as a result of performing similar tests using evaluation samples having dilution ratios of 0.1% and 1%, a tendency similar to the above case of 0.01% was obtained. However, it has been suggested that in the odorant compositions of Examples 1 to 4, it is more preferable to set the dilution ratio to about 0.01%.

Note that the evaluation items (words) in the sensory evaluations 1 and 2 were selected under advice of a clinical psychologist. The same applies to sensory evaluation described later.

<Formulation with 15 Compounds>

[Preparation of Odorant Composition]

Chemical compounds were blended according to blending ratios (% by mass) of Formulation Nos. 1501 to 1532 described in Tables 12-1 and 12-2 above to prepare 19 kinds in total of odorant compositions of Examples 1501 to 1532.

[Sensory Evaluation of Scent of Odorant Composition]

A solution was prepared by diluting each of the odorant compositions of Examples 1501 to 1532 to 0.1% with propylene glycol, and used as an evaluation sample. Each evaluation sample was immersed in filter paper, and for an impression of sniffing the scent, a sensory evaluation test was performed in which the degree of feeling that the scent fell under each of evaluation items described in Table 18 below was evaluated by 20 (Japanese) subjects in 11 stage of 0 point (a subject does not think at all that the sample is so) to 10 points (a subject completely thinks that the sample is so).

TABLE 18

| Symbol | Item |
| --- | --- |
| t1 | likable |
| t2 | strong |
| t3 | pungent |
| t4 | mild |
| t5 | mellow |
| t6 | rich |
| t7 | sweet |
| t8 | memorable |
| t9 | fermented |
| t10 | astringent |
| t11 | medicinal |
| t12 | pleasant |
| t13 | fatty |
| t14 | milky |
| t15 | alcoholic |
| t16 | floral |
| t17 | subtle |
| t18 | fruity |
| t19 | stinky |
| t20 | warm |
| t21 | cool |
| t22 | relaxing |
| t23 | foresty |
| t24 | earthy |
| t25 | disliked |
| t26 | green |
| t27 | musty |
| t28 | want to protect |
| t29 | beast-like |
| t30 | unpleasant |
| t31 | detergent-like |
| t32 | solvent-like |
| t33 | acquired |
| t34 | addictive |
| t35 | heavy |
| t36 | happy |
| t37 | nauseous |
| t38 | unforgettable |
| t39 | overcast |
| t40 | sweaty |
| t41 | refreshing |
| t42 | tobacco-like |
| t43 | enchanting |
| t44 | powdery |
| t45 | overwhelming |
| t46 | citrus |
| t47 | fecal |
| t48 | positive |
| t49 | sour/acidic |
| t50 | affectionate |

Figure 3:
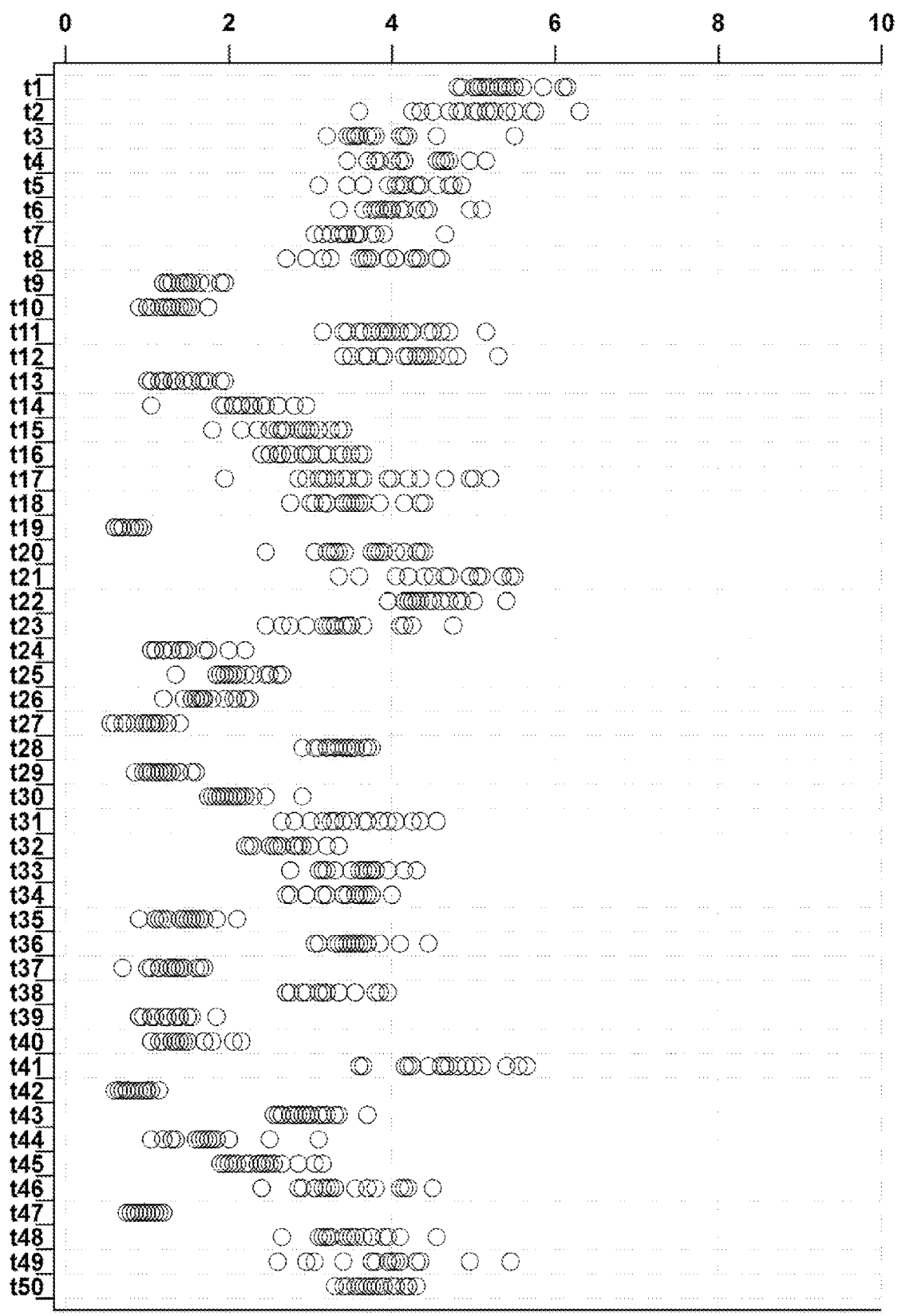
FIG. 3 is a graph showing results of sensory evaluation of scents of odorant compositions of Examples 1501 to 1532.

Results thereof are summarized in FIG. 3.

FIG. 3 is a graph showing results of sensory evaluation of scents of the odorant compositions of Examples 1501 to 1532.

In FIG. 3, an average value (horizontal axis) of results (scores) obtained for each evaluation item (vertical axis) is plotted on one graph for each odorant composition.

As shown in FIG. 3, for all the evaluation samples of the odorant compositions of Examples 1501 to 1532, scores for the item "likable" are concentrated in the vicinity of about 5 to 6 points and higher than scores for the other evaluation items, and vary slightly depending on a sample. In addition, scores in a range of approximately 4 points to 6 points are obtained for the items "refreshing" and "relaxing". In addition, scores for the items "mild", "mellow", "pleasant", "cool", "happy", "positive", and "affectionate" fall within a range centered on 4 points, and scores for the items "want to protect" and "enchanting" fall within a range of approximately 3 points to 4 points and vary only slightly.

Figure 4:
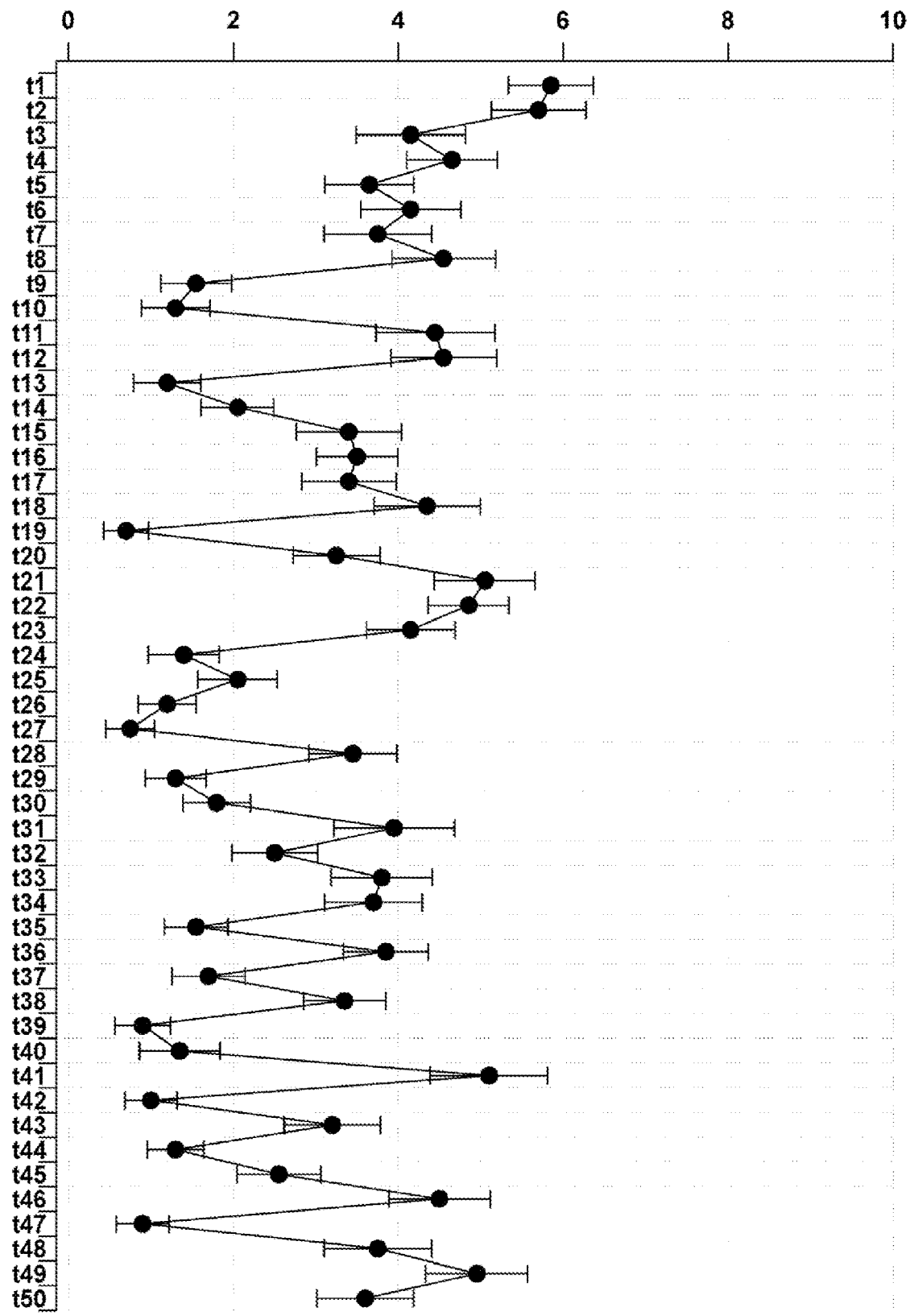
FIG. 4 is a graph showing results of sensory evaluation of a scent of an odorant composition of Example 1502.
Figure 5:
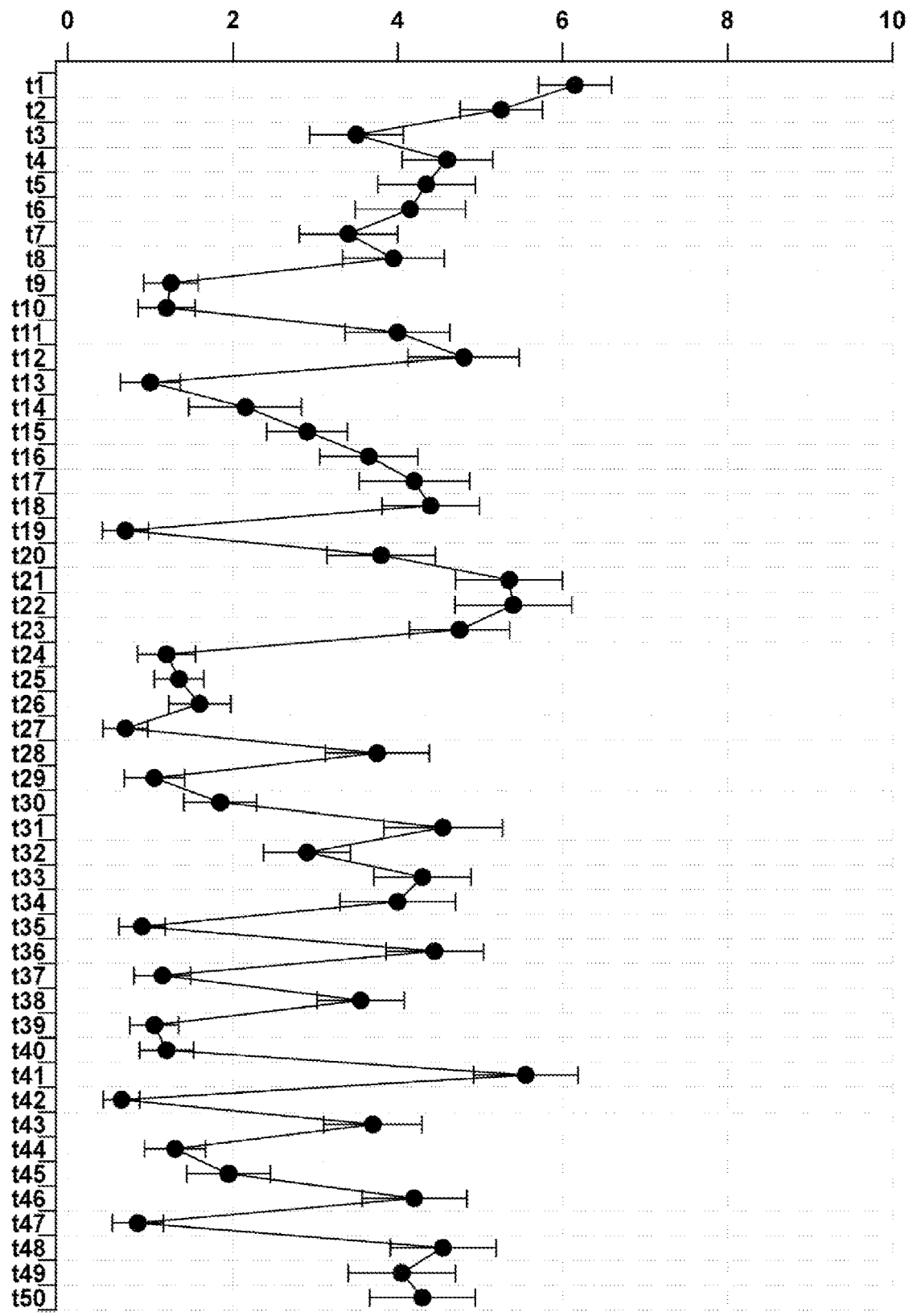
FIG. 5 is a graph showing results of sensory evaluation of a scent of an odorant composition of Example 1505.
Figure 6:
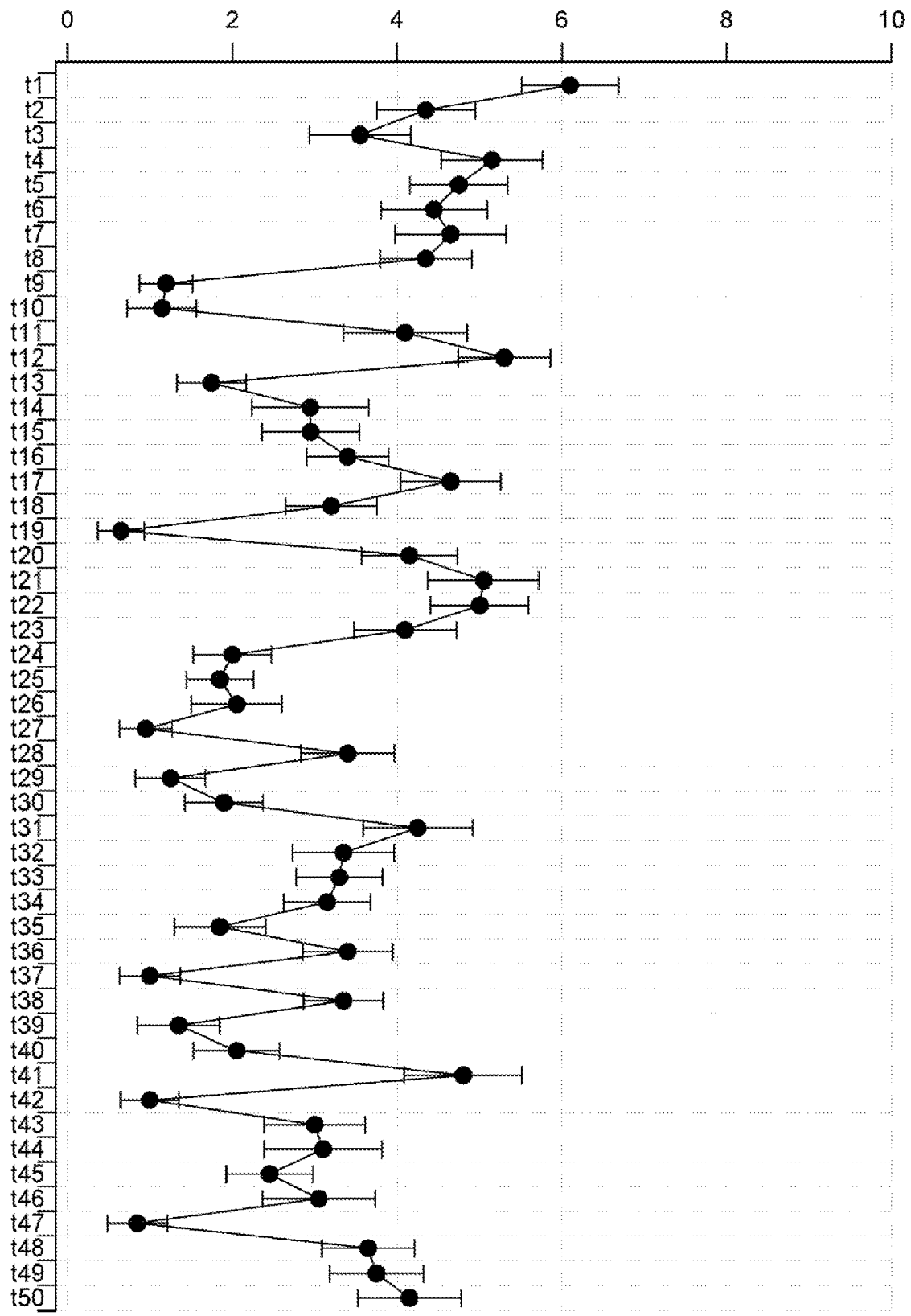
FIG. 6 is a graph showing results of sensory evaluation of a scent of an odorant composition of Example 1530.

FIGS. 4 to 6 each show an example of results for an evaluation sample.

FIG. 4 is a graph showing results of sensory evaluation of a scent of the odorant composition of Example 1502.

FIG. 5 is a graph showing results of sensory evaluation of a scent of the odorant composition of Example 1505.

FIG. 6 is a graph showing results of sensory evaluation of a scent of the odorant composition of Example 1530.

From the results shown in FIGS. 4 to 6, it can be seen that there is a tendency that scores are high for words indicating a positive impression or emotion (positive words) as described above for FIG. 3, and scores are low for words indicating a negative impression or emotion (negative words) such as "disliked", "unpleasant", "pungent", "astringent", "earthy", "musty", and "beast-like".

From these results, it has been suggested that the odorant compositions of Examples 1501 to 1532 have good scent palatability, allow a person to feel comfortable, and/or can enhance a positive emotion of a person who has smelled the scent.

In addition, as a result of an statistical analysis uniquely found by the present inventors, in which the scores for the individual evaluation items are statistically analyzed using a correlation coefficient obtained by taking a relevance among the evaluation items into account, it has been found that the effects of the odorant compositions of Examples 1501 to 1532 described above can be supported. In particular, according to this statistical analysis, it has been suggested that the formulations belonging to the lines "02", "05", and "30" provide odorant compositions that can exhibit more favorable effects.

It should be noted that, among the evaluation items, the tendency of having a high score for "strong" or "rich" is not necessarily a negative result because there may be an influence of a distance between a subject's nose and filter paper when the subject sniffs a scent.

[Sensory Evaluation by Subjects of Different Nationalities]

Next, a sensory evaluation test was performed by subjects of various nationalities using an evaluation sample having a dilution ratio of 0.1% of the odorant composition of Example 1510 prepared in a similar manner to the sensory evaluation described above. The subjects included 36 Japanese, 13 Polish, 5 Taiwanese, and 2 Indians.

Note that a reason why the odorant composition of Example 1510 was used as the evaluation sample of the present test is that among Examples 1501 to 1532 described above, Example 1510 had an approximately average result (score) for all the evaluation items, and therefore was considered to be appropriate to test scent palatability of a subject of a nationality other than Japan.

Results thereof are shown in FIGS. 7 to 10.

Figure 7:
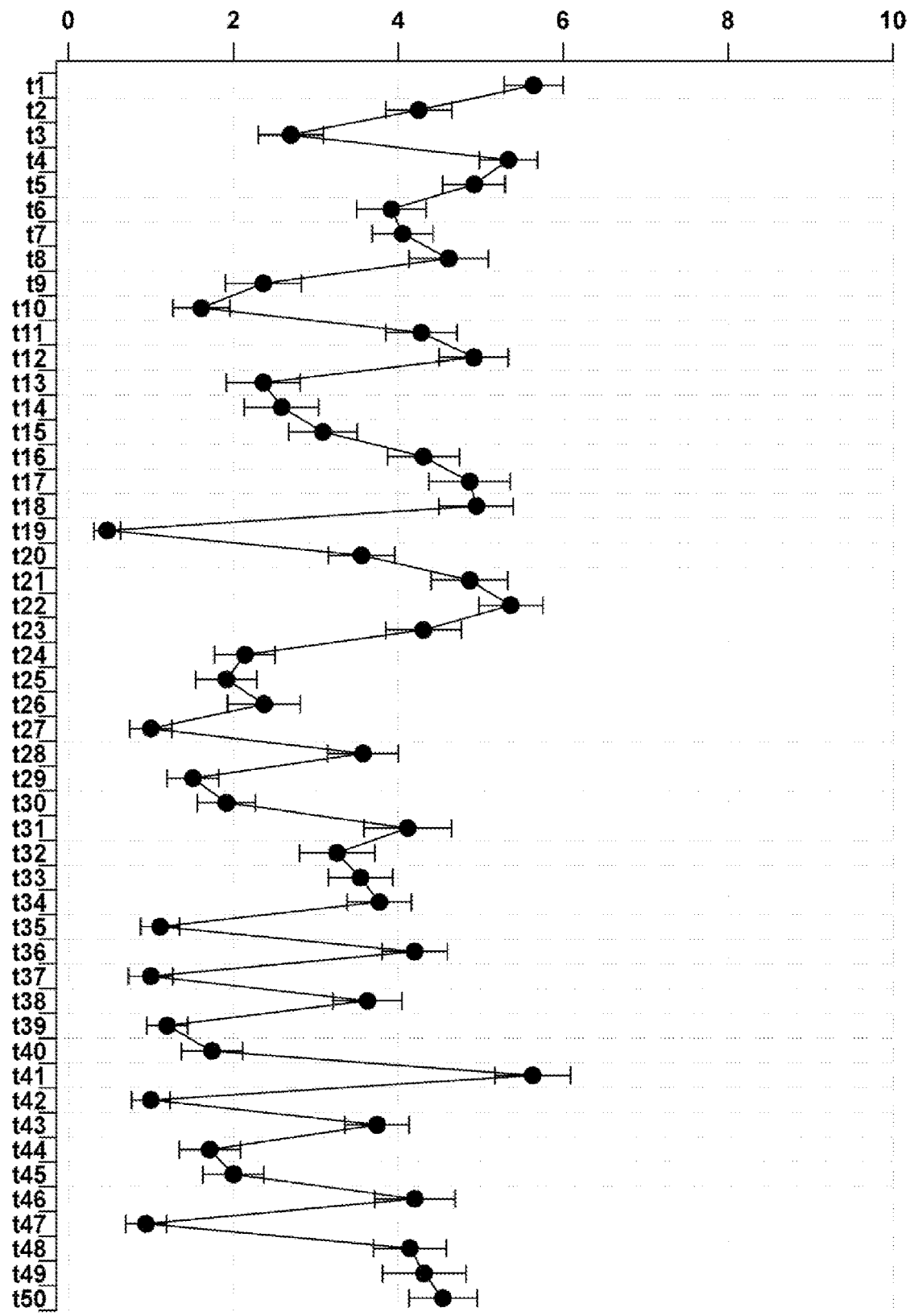
FIG. 7 is a graph showing results of sensory evaluation of a scent of an odorant composition of Example 1510 by Japanese subjects.

FIG. 7 is a graph showing results of sensory evaluation of a scent of the odorant composition of Example 1510 by Japanese subjects.

Figure 8:
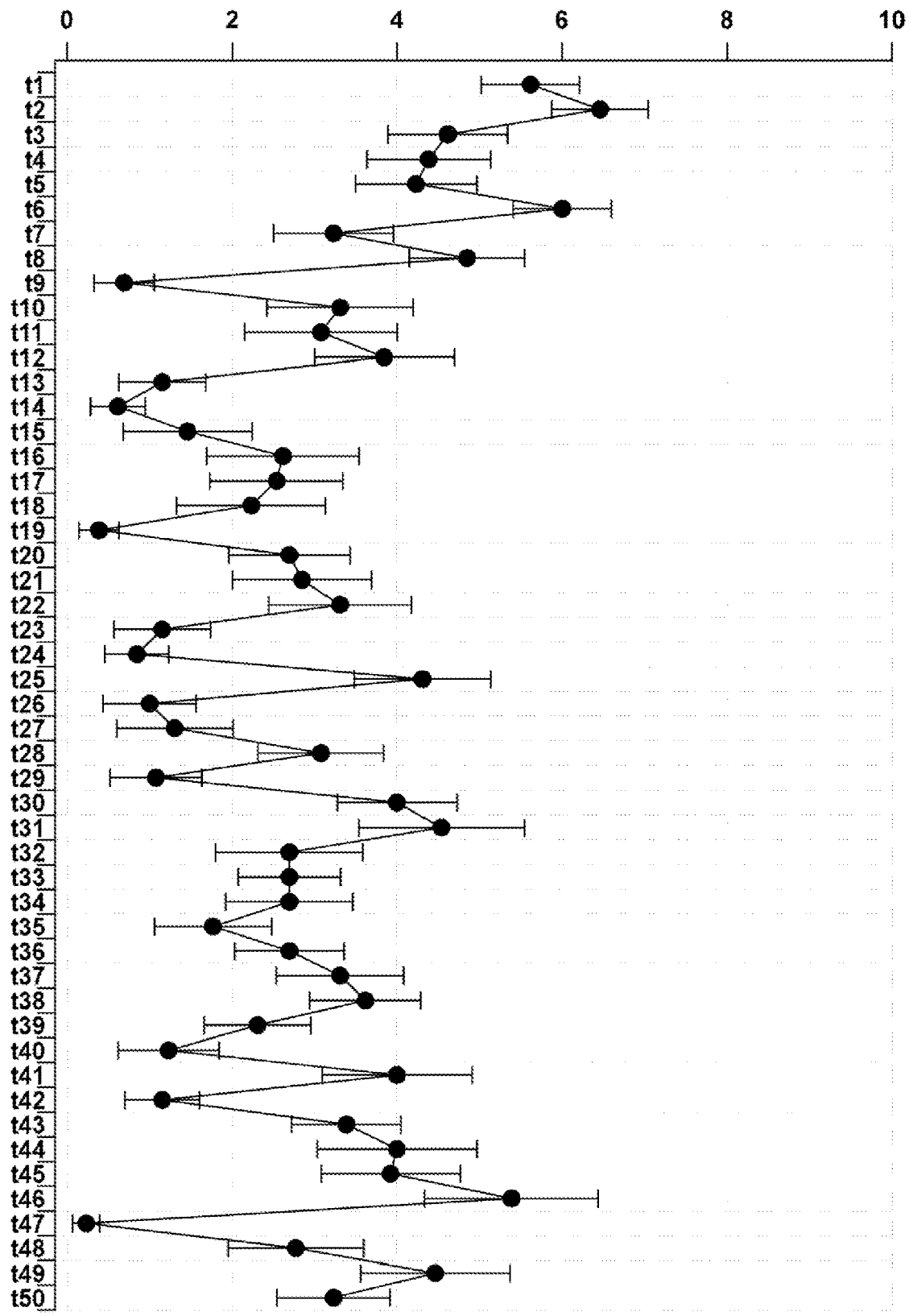
FIG. 8 is a graph showing results of sensory evaluation of the scent of the odorant composition of Example 1510 by Polish subjects.

FIG. 8 is a graph showing results of sensory evaluation of the scent of the odorant composition of Example 1510 by Polish subjects.

Figure 9:
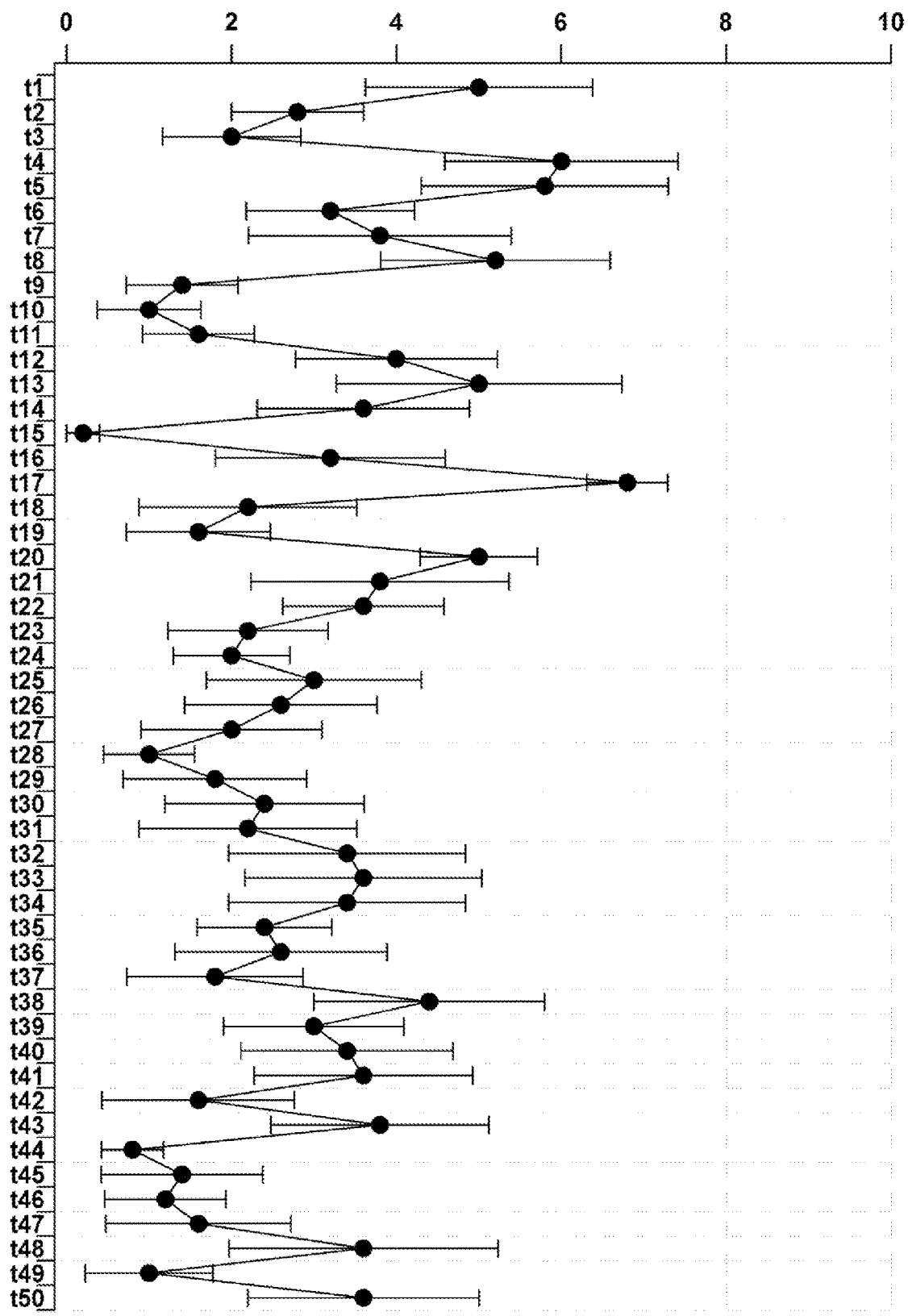
FIG. 9 is a graph showing results of sensory evaluation of the scent of the odorant composition of Example 1510 by Taiwanese subjects.

FIG. 9 is a graph showing results of sensory evaluation of the scent of the odorant composition of Example 1510 by Taiwanese subjects.

Figure 10:
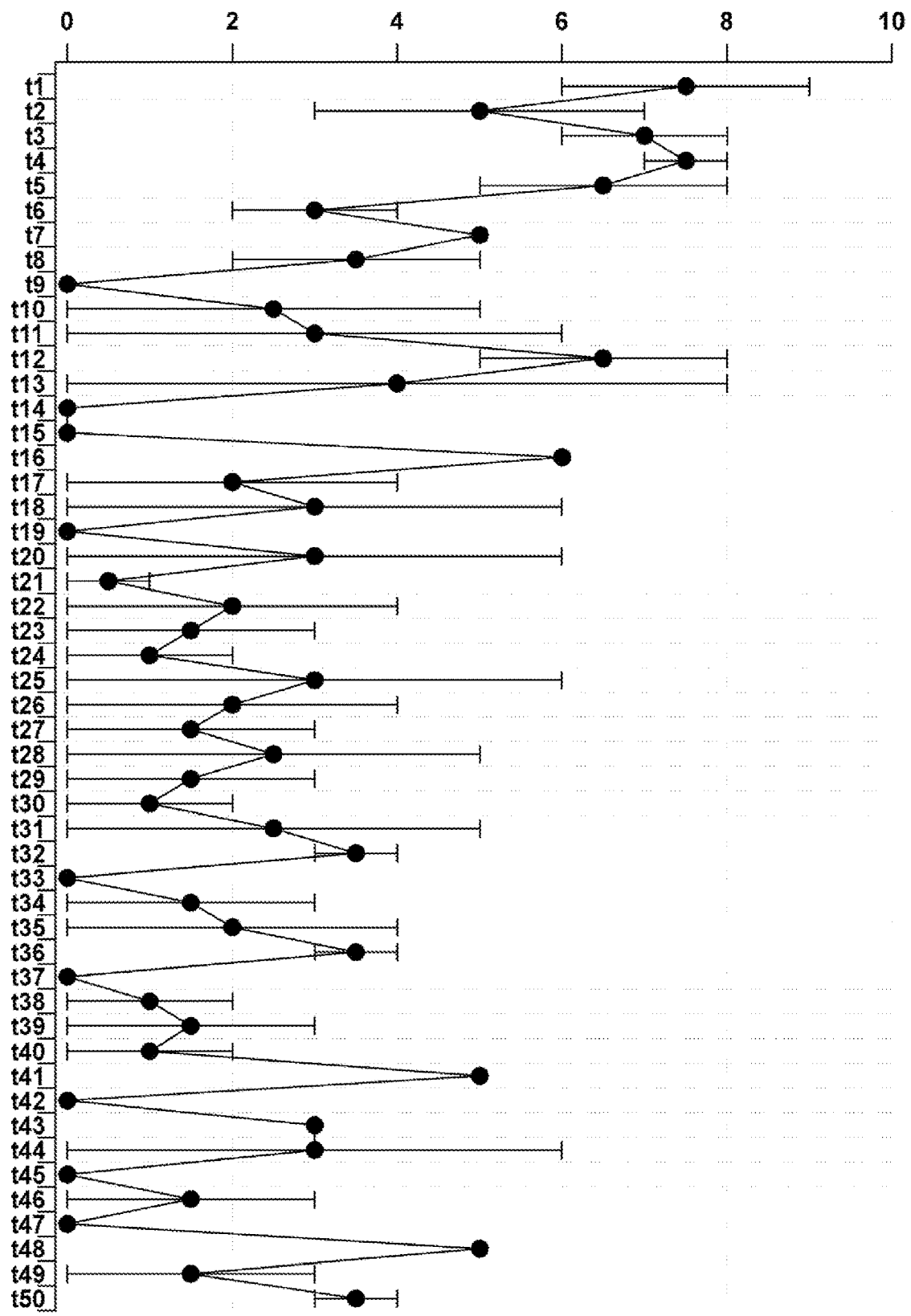
FIG. 10 is a graph showing results of sensory evaluation of the scent of the odorant composition of Example 1510 by Indian subjects.

FIG. 10 is a graph showing results of sensory evaluation of the scent of the odorant composition of Example 1510 by Indian subjects.

As shown in FIGS. 7 to 10, there was a tendency that an impression or feeling on the same evaluation sample slightly differed depending on the nationality of a subject, but as represented by a high score for the item "likable" in all the subjects, it has been suggested that the odorant composition of the present invention is a favorable scent regardless of the nationality.

<Formulation with Eight Compounds>
[Preparation of Odorant Composition]

Chemical compounds were blended according to blending ratios (% by mass) of Formulation No. 802 described in Table 14-1 above to prepare an odorant composition of Example 802.

[Sensory Evaluation of Scent of Odorant Composition]

An evaluation sample having a dilution ratio of 0.1% of the odorant composition of Example 802 was prepared by a similar procedure to that described above for Examples 1501 to 1532, and a sensory evaluation test was performed by 10 (Japanese) subjects.

Figure 11:
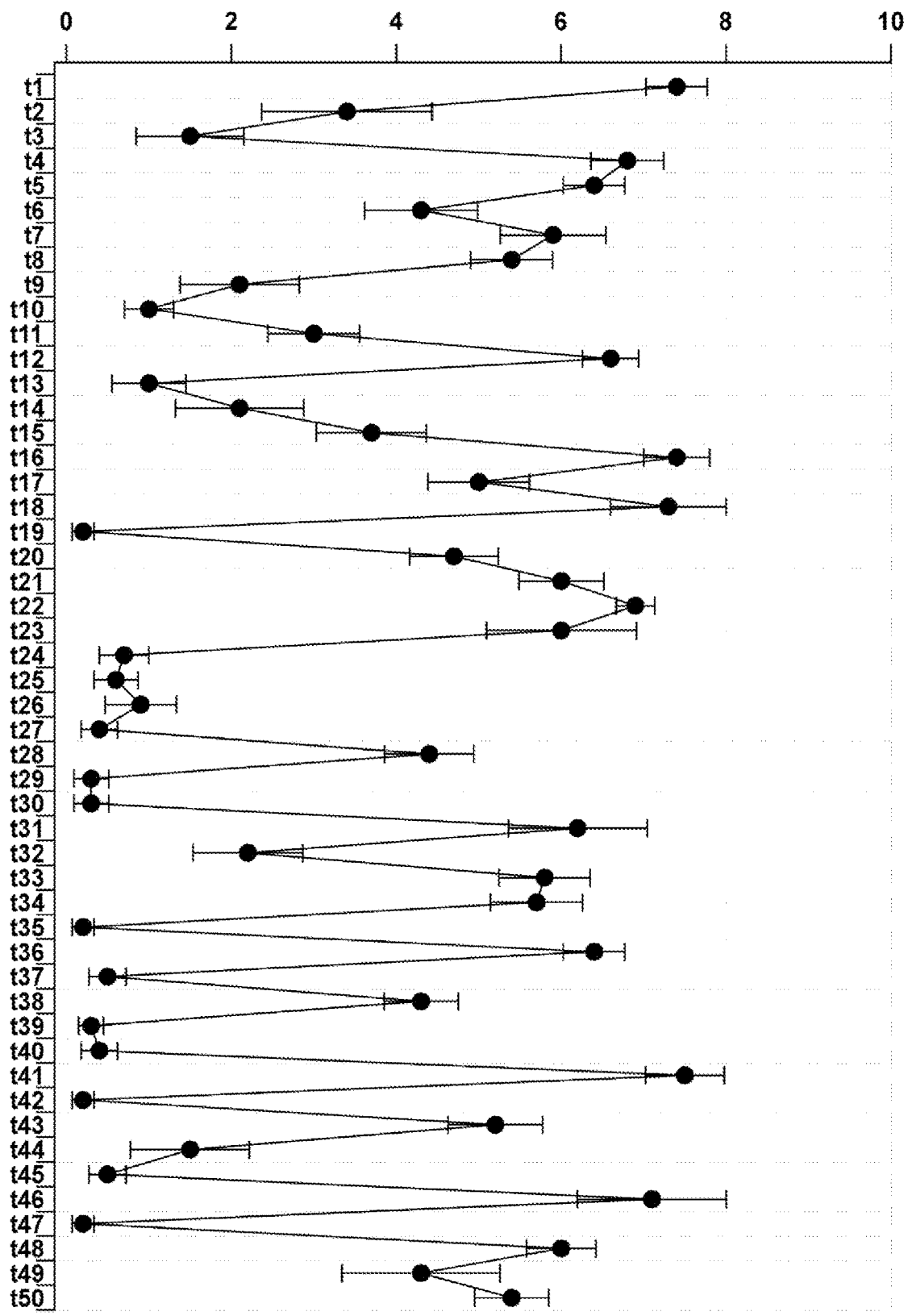
FIG. 11 is a graph showing results of sensory evaluation of a scent of an odorant composition of Example 802.

Results thereof are shown in FIG. 11.

FIG. 11 is a graph showing results of sensory evaluation of a scent of the odorant composition of Example 802.

From the results shown in FIG. 11, it has been confirmed that the odorant composition of Example 802 has a similar tendency to the results obtained using the odorant compositions of Examples 1501 to 1532 described above (see FIGS. 3 to 6).

In particular, as compared with the result of Example 1502 (FIG. 4) prepared based on Formulation No. 1502 belonging to the same line as Formulation No. 802, it can be seen that the odorant composition of Example 802 has a larger difference between a score for a positive word and a score for a negative word, and provides a sharper result. In addition, it should be noted that, in both Example 802 (FIG. 11) and Example 1502 (FIG. 4), the scores for the items "likable" and "pleasant" are obviously higher than the scores for the items "disliked" and "unpleasant".

[Comparison Test with Odorant Compositions Having Various Compositions]

Next, an evaluation sample having a dilution ratio of 0.1% of an odorant composition prepared by blending chemical compounds according to blending ratios (% by mass) of the odorant composition of Example 802 and Comparative Example 1 to 4 described in Table 19 below was prepared, and a sensory evaluation test was performed by 10 (Japanese) subjects by a similar procedure to that described above for Examples 1501 to 1532.

TABLE 19

| Ingredient | Chemical Compound | Example 802 | Compar. Ex. 1 | Compar. Ex. 2 | Compar. Ex. 3 | Compar. Ex. 4 |
|---|---|---|---|---|---|---|
| A2 | Hexanal | 0 | 0 | 0 | 0 | 0 |
| A2 | Heptanal | 0 | 0 | 0 | 0 | 0 |
| A2 | Benzaldehyde | 2.5 | 8.5 | 2.7 | 2.8 | 3.0 |
| B | 6-Methyl-5-hepten-2-one | 9.0 | 31.4 | 0.0 | 10.2 | 1.0 |
| A2 | Octanal | 0.0 | 0.0 | 0.0 | 0.0 | 0.0 |
| C | Hexanoic acid | 0.0 | 0.0 | 0.0 | 0.0 | 0.0 |
| C | p-Cymene | 0.0 | 0.0 | 0.0 | 0.0 | 0.0 |
| C | 1,8-Cineole | 4.3 | 15.0 | 4.7 | 0.0 | 0.4 |
| C | Limonene | 3.1 | 10.7 | 3.4 | 0.0 | 0.2 |
| B | 1-Phenylethanone | 0.0 | 0.0 | 0.0 | 0.0 | 0.0 |
| A1 | Nonanal | 54.5 | 0.0 | 59.9 | 61.3 | 66.9 |
| C | 2-Nonen-1-ol | 0.0 | 0.0 | 0.0 | 0.0 | 0.0 |
| C | Menthol | 3.7 | 13.0 | 4.1 | 0.0 | 0.4 |
| B | 2-Decanone | 0.0 | 0.0 | 0.0 | 0.0 | 0.0 |
| A2 | Decanal | 16.8 | 0.0 | 18.5 | 18.9 | 20.7 |
| C | Octanoic acid | 0.0 | 0.0 | 0.0 | 0.0 | 0.0 |
| B | 2-Undecanone | 0.0 | 0.0 | 0.0 | 0.0 | 0.0 |
| C | Nonanoic acid | 0.0 | 0.0 | 0.0 | 0.0 | 0.0 |
| A2 | Undecanal | 6.1 | 21.3 | 6.7 | 6.9 | 7.5 |
| | Total | 100.0 | 100.0 | 100.0 | 100.0 | 100.0 |

Figure 12:
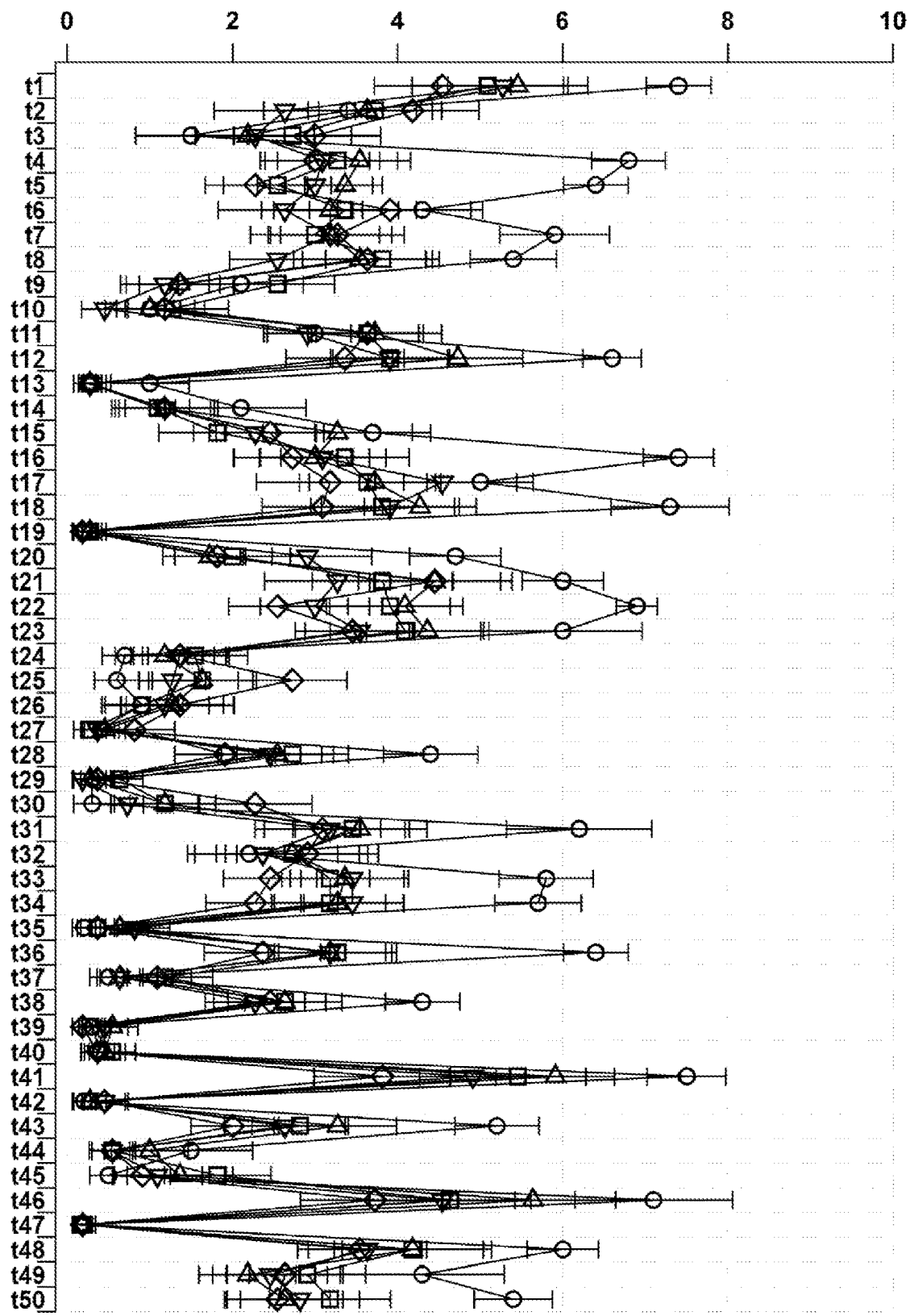
FIG. 12 is a graph showing results of sensory evaluation of scents of odorant compositions of Example 802 and Comparative Example 1 to 4.

Results thereof are summarized in FIG. 12.

FIG. 12 is a graph showing results of sensory evaluation of scents of odorant compositions of Example 802 and Comparative Example 1 to 4.

In FIG. 12, Example 802 is indicated by a circle, Comparative Example 1 is indicated by an upward triangle, Comparative Example 2 is indicated by a square, Comparative Example 3 is indicated by a rhombus, and Comparative Example 4 is indicated by a downward triangle.

From the results shown in FIG. 12, it can be seen that in the odorant composition of Example 802, scores for the items "likable", "mild", "mellow", "sweet", "pleasant", "floral", "fruity", "warm", "cool", "foresty", and "refreshing" are significantly higher than scores in the odorant compositions of Comparative Examples 1 to 4. In addition, in the odorant composition of Example 802, scores for the items "relaxing", "want to protect", "addictive", "happy", "unforgettable", "positive", and "affectionate" are also significantly higher than scores in the odorant compositions of Comparative Examples 1 to 4. It should be noted that all of the above items are words (positive words) indicating a positive impression or emotion of a person who has smelled the scent.

[Comparison Test with Commercially Available Perfume]

Next, an evaluation sample having a dilution ratio of 0.1% of the odorant composition of Example 802 and evaluation samples of three kinds of commercially available perfumes were prepared, and a sensory evaluation test was performed by 10 (Japanese) subjects by a similar procedure to that described above for Examples 1501 to 1532.

The perfumes used in this test were perfume 1 (product name "Petits et Mamans" manufactured by BVLGARI), perfume 2 (product name "Baby Powder" manufactured by DEMETER), and perfume 3 (product name "Creature d Anges" manufactured by Creature). As a result of analysis with a gas chromatograph mass spectrometer (GC-MS), the numbers of chemical compounds detected and identified in the perfumes 1, 2, and 3 were 24, 24, and 43, respectively. Note that in each of the perfumes 1 to 3, there is a compound that has been difficult to identify from the obtained chromatogram and mass spectrum, and therefore it is considered that the number of chemical compounds actually contained is larger than the above.

Figure 13:
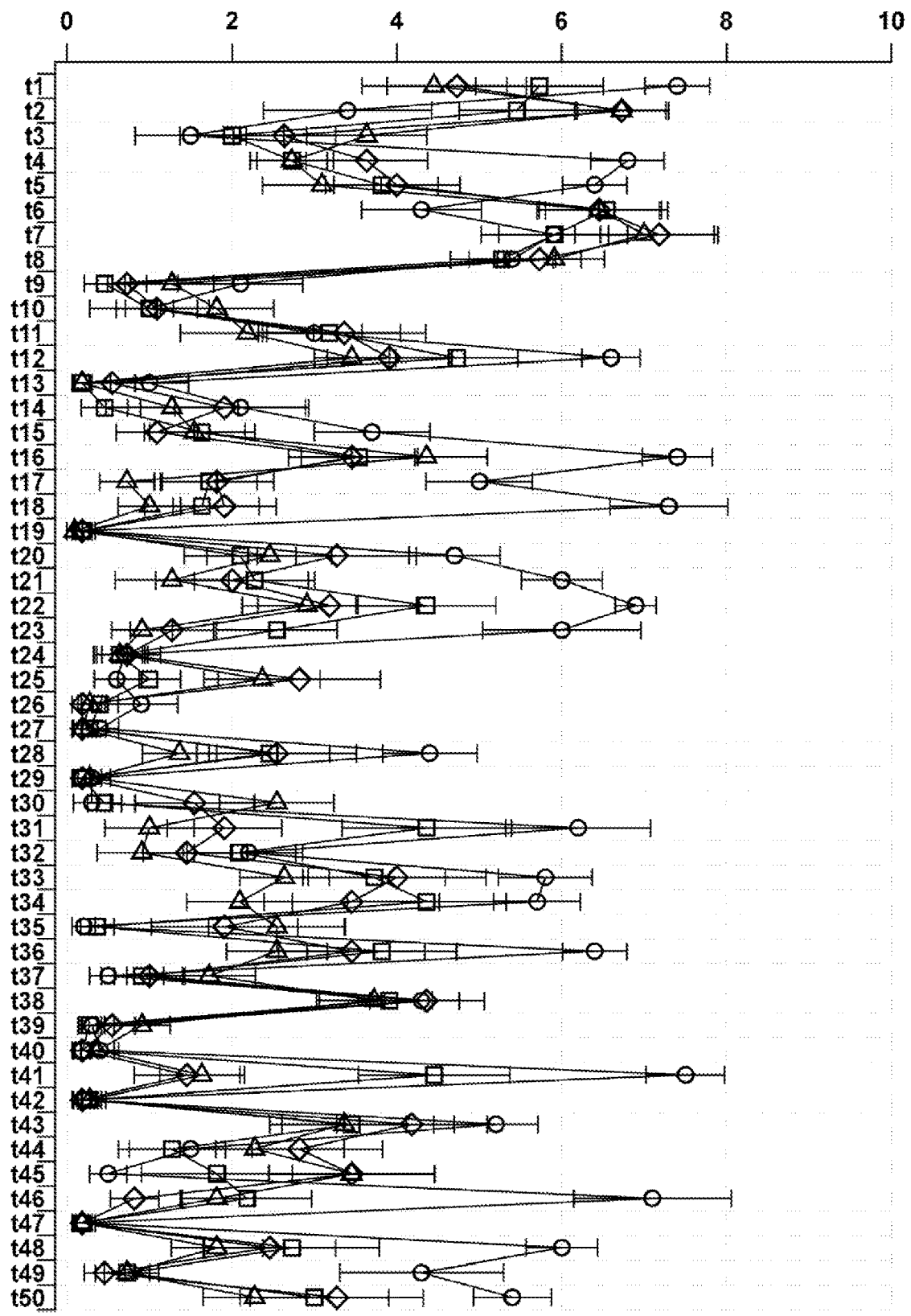
FIG. 13 is a graph showing results of sensory evaluation of scents of the odorant composition of Example 802 and commercially available perfumes 1 to 3.

Results thereof are summarized in FIG. 13.

FIG. 13 is a graph showing results of sensory evaluation of scents of the odorant composition of Example 802 and the commercially available perfumes 1 to 3.

In FIG. 13, Example 802 is indicated by a circle, the perfume 1 is indicated by an upward triangle, the perfume 2 is indicated by a rhombus, and the perfume 3 is indicated by a square.

From the results shown in FIG. 13, it can be seen that in the odorant composition of Example 802, scores for the items "likable", "mild", "mellow", "pleasant", "floral", "subtle", "fruity", "warm", "cool", "foresty", and "refreshing" are significantly higher than scores in the perfumes 1 to 3. In addition, in the odorant composition of Example 802, scores for the items "relaxing", "want to protect", "addictive", "happy", "positive", and "affectionate" are also significantly higher than scores in the perfumes 1 to 3. It should be noted that all of the above items are words (positive words) indicating a positive impression or emotion of a person who has smelled the scent.

<Formulation with Nine Compounds>
[Preparation of Odorant Composition]

Chemical compounds were blended according to blending ratios (% by mass) of Formulation No. 902 described in Table 13-1 above and Formulation No. 913 described in Tables 13-2 above to prepare odorant compositions of Examples 902 and 913.

[Sensory Evaluation of Scent of Odorant Composition]

An evaluation sample having a dilution ratio of 0.1% of each of the odorant compositions of Examples 902 and 913 was prepared by a similar procedure to that described above for Examples 1501 to 1532, and a sensory evaluation test was performed by 11 (Japanese) subjects.

Figure 14:
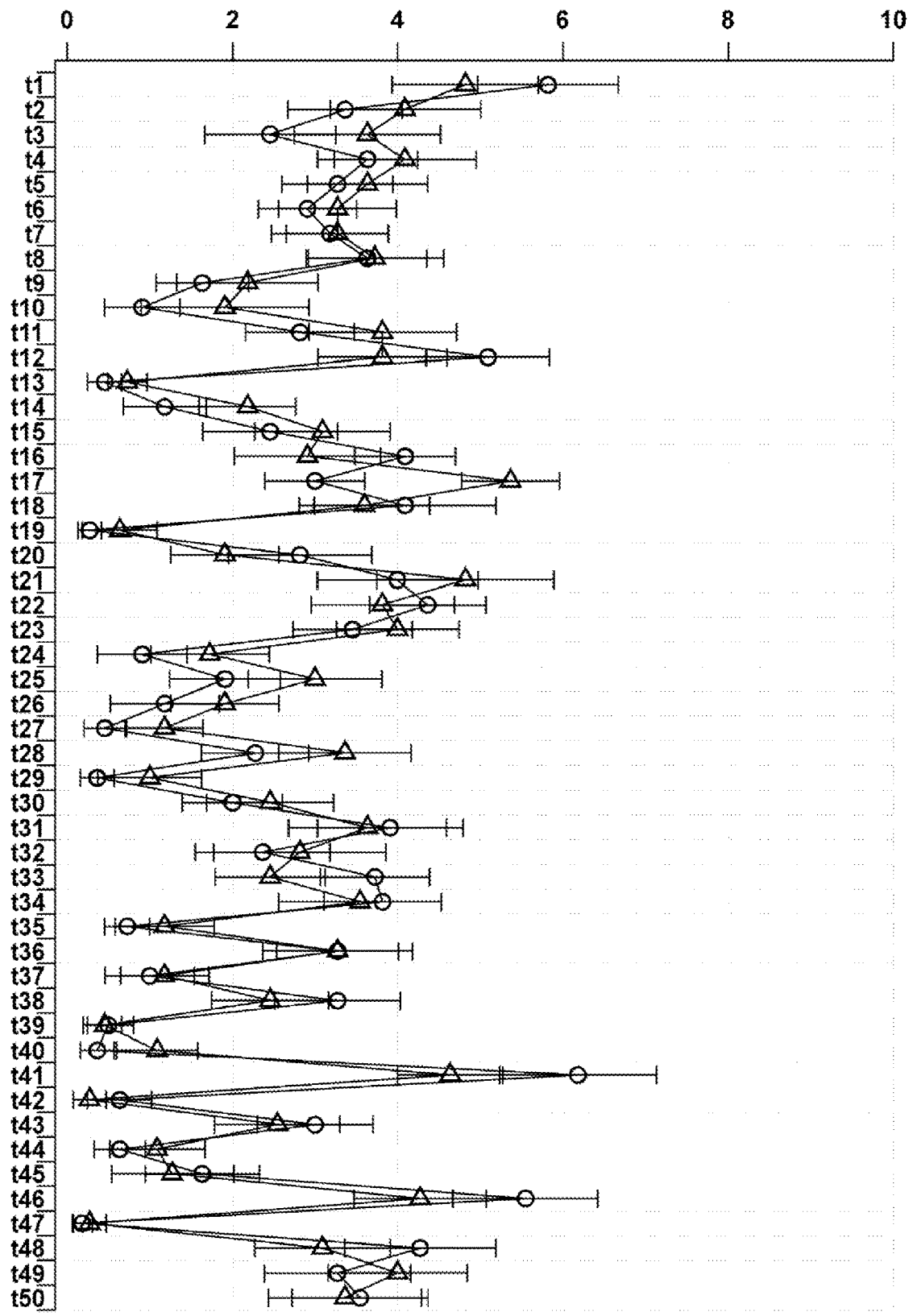
FIG. 14 is a graph showing results of sensory evaluation of scents of odorant compositions of Examples 902 and 913.

Results thereof are summarized in FIG. 14.

FIG. 14 is a graph showing results of sensory evaluation of scents of the odorant compositions of Examples 902 and 913.

In FIG. 14, Example 902 is indicated by a circle, and Example 913 is indicated by an upward triangle.

From the results shown in FIG. 14, it can be seen that the odorant composition of Example 902 and the odorant composition of Example 913 generally have similar scent tendencies to each other. In addition, particularly in the odorant composition of Example 902, there was a tendency that scores for the items "likable", "pleasant", and "refreshing" were higher than scores in the odorant composition of Example 913.

INDUSTRIAL APPLICABILITY

The odorant composition of the present invention is prepared using a smaller number of chemical compounds than a conventional odorant composition, and therefore can be manufactured by a simple method, which is advantageous in terms of manufacturing cost. In addition, the odorant composition of the present invention has good palatability allowing peoples to feel comfortable. In addition, the odorant composition of the present invention can enhance a positive emotion of a person who has smelled a scent of the odorant composition. The odorant composition of the present invention having such an effect is blended in perfumery and cosmetics, food and drink, a tobacco product, an ink, a drawing material, and the like, and used for various materials such as a wrapping and packaging material and a toy, thereby enhancing commercial values thereof.

The invention claimed is:

1. An odorant composition consisting of: when a total mass of ingredients contained in the odorant composition is 100.0% by mass,
   75.0% by mass or more and 95.0% by mass or less of an ingredient (A) composed of aldehydes;
   1.0% by mass or more and 20.0% by mass or less of an ingredient (B) composed of a ketone(s); and
   the balance being an ingredient (C) composed of a chemical compound(s) other than the ingredient (A) and the ingredient (B), wherein
   the aldehydes of the ingredient (A) are:
      an essential ingredient (A1) composed of nonanal; and
      an optional ingredient (A2) selected from the group consisting of decanal, heptanal, octanal, benzaldehyde, undecanal, hexanal, and combinations thereof,
   a content of the essential ingredient (A1) is 27.0% by mass or more and 64.0% by mass or less,
   the ketone(s) of the ingredient (B) is selected from the group consisting of 6-methyl-5-hepten-2-one, cyclohexanone, 1-phenylethanone, 2-decanone, 2-undecanone, and combinations thereof, and
   the chemical compound(s) of the ingredient (C) is selected from the group consisting of limonene, 1,8-cineole, menthol, 1-octanol, 3-hexyn-1-ol, 2-nonen-1-ol, dodecane, hexanoic acid, octanoic acid, nonanoic acid, 2 (5H)-furanone, p-cymene, sotolon, and combinations thereof.

2. The odorant composition according to claim 1, wherein the ingredient (B) is selected from the group consisting of 6-methyl-5-hepten-2-one, 1-phenylethanone, 2-decanone, 2-undecanone, and combinations thereof, and the ingredient (C) is selected from the group consisting of limonene, 1,8-cineole, menthol, 2-nonen-1-ol, hexanoic acid, octanoic acid, nonanoic acid, p-cymene, and combinations thereof.

3. The odorant composition according to claim 2, wherein the content of the essential ingredient (A1) is 43.0% by mass or more and 62.0% by mass or less, and a content of the ingredient (B) is 1.0% by mass or more and 12.0% by mass or less.

4. The odorant composition according to claim 3, wherein the content of the ingredient (A) is 75.0% by mass or more and 80.0% by mass or less,
   the content of the essential ingredient (A1) is 48.0% by mass or more and 55.0% by mass or less,
   the content of the ingredient (B) is 8.0% by mass or more and 11.0% by mass or less,
   the ingredient (B) is 6-methyl-5-hepten-2-one or a combination of 6-methyl-5-hepten-2-one, 1-phenylethanone, and 2-decanone, and
   the ingredient (C) is a combination of limonene, 1,8-cineole, and menthol, a combination of limonene, 1,8-cineole, menthol, and p-cymene, or a combination of limonene, 1,8-cineole, menthol, 2-nonen-1-ol, and p-cymene.

5. The odorant composition according to claim 3, wherein the content of the ingredient (A) is 81.0% by mass or more and 85.0% by mass or less,
   the content of the essential ingredient (A1) is 58.0% by mass or more and 62.0% by mass or less,
   the content of the ingredient (B) is 8.0% by mass or more and 10.0% by mass or less,
   the ingredient (B) is a combination of 6-methyl-5-hepten-2-one and 1-phenylethanone or a combination of 6-methyl-5-hepten-2-one, 1-phenylethanone, and 2-decanone, and the ingredient (C) is a combination of limonene and menthol, a combination of limonene, 1,8-cineole, and menthol, or a combination of limonene, 1,8-cineole, menthol, 2-nonen-1-ol, and nonanoic acid.

6. The odorant composition according to claim 3, wherein
the content of the ingredient (A) is 81.0% by mass or more and 85.0% by mass or less,
the content of the essential ingredient (A1) is 58.0% by mass or more and 62.0% by mass or less,
the content of the ingredient (B) is 2.0% by mass or more and 5.0% by mass or less,
the ingredient (B) is 6-methyl-5-hepten-2-one, a combination of 6-methyl-5-hepten-2-one and 1-phenylethanone, or a combination of 6-methyl-5-hepten-2-one, 1-phenylethanone, 2-decanone, and 2-undecanone, and
the ingredient (C) is a combination of limonene, menthol, and 2-nonen-1-ol or a combination of limonene, 1,8-cineole, menthol, 2-nonen-1-ol, and p-cymene.

7. A product comprising the odorant composition according to claim 1, the product being selected from the group consisting of perfumery and cosmetics, food and drink, and a tobacco product.

8. A microcapsule or a nanocapsule comprising the odorant composition according to claim 1.

9. An ink comprising the microcapsule or the nanocapsule according to claim 8.

10. A printed matter using the ink according to claim 9.

11. A drawing material comprising the microcapsule or the nanocapsule according to claim 8.

12. A material using the odorant composition according to claim 1.

13. The material according to claim 12, which is paper, a fabric, a woven fabric, a knitted fabric, a nonwoven fabric, a rug, a plate material, an ornament, a wrapping and packaging material, or a toy.

* * * * *